(12) United States Patent
Harner et al.

(10) Patent No.: US 7,843,560 B2
(45) Date of Patent: Nov. 30, 2010

(54) STABLE TURBIDITY CALIBRATION STANDARDS

(75) Inventors: Richard S. Harner, Midland, MI (US); J. Keith Harris, Midland, MI (US); William A. Heeschen, Midland, MI (US); Mary Beth Seasholtz, Sanford, MI (US)

(73) Assignee: Dow Global Technologies Inc., Midland, MI (US)

( * ) Notice: Subject to any disclaimer, the term of this patent is extended or adjusted under 35 U.S.C. 154(b) by 312 days.

(21) Appl. No.: 12/195,779

(22) Filed: Aug. 21, 2008

(65) Prior Publication Data

US 2009/0059218 A1    Mar. 5, 2009

Related U.S. Application Data

(60) Provisional application No. 60/969,213, filed on Aug. 31, 2007.

(51) Int. Cl.
*G01J 1/10* (2006.01)

(52) U.S. Cl. .................... 356/243.2; 356/442

(58) Field of Classification Search .............. 356/243.2, 356/432–444, 36–38; 526/160, 170, 127, 526/348.1, 348.7–348.8, 126, 131, 943; 525/240, 77–86
See application file for complete search history.

(56) References Cited

U.S. PATENT DOCUMENTS

| | | | |
|---|---|---|---|
| 2,471,959 A | 5/1949 | Hunt | |
| 3,113,114 A | 12/1963 | Maginn et al. | |
| 5,272,236 A | 12/1993 | Lai et al. | |
| 5,278,272 A | 1/1994 | Lai et al. | |
| 5,324,802 A | 6/1994 | Krieg | |
| 5,665,800 A | 9/1997 | Lai et al. | |
| 7,217,763 B2 | 5/2007 | Choi et al. | |

FOREIGN PATENT DOCUMENTS

WO    WO 2004/053468    6/2004

OTHER PUBLICATIONS

Cantow Manfred J.R., "Turbidimetric Titration", Polymer Fractionation, 1967, 191-211, Academic Press.

J. T. Cabral et al, "Discrete combinatorial investigation of polymer mixture phase boundaries", Measurement Science and Technology, 2005, 191-198, vol. 16, No. 1, IOP Publishing Ltd.

G. Chawla et al, "High-throughput Polymorph Screening of Pharmaceutical-'Farming for Crystal Mutants'", Screening & Image Analysis, Business Briefing: Future Drug Discovery, 2004, 66-72.

Jose et al., "Automated Image Analysis of Polymer Beads and Size Distribution", Industrial & Engineering Chemistry Research, 2005, 8659-8662, vol. 44, American Chemical Society.

(Continued)

*Primary Examiner*—Gregory J Toatley
*Assistant Examiner*—Tri T Ton
(74) *Attorney, Agent, or Firm*—Claude F. Purchase; Dan R. Howard; The Dow Chemical Company

(57) ABSTRACT

The present invention relates to a turbidity calibration standard comprising: a number of from 1 to 5 sequentially-interfaced layers, wherein each layer independently comprises a light-permeable polymer or light-permeable interpolymer; a measured light transmission modulating amount of at least one light transmission modulator, which is distributed in any one or more of the layers; and a light-permeable container, which contains the layers and the at least one light transmission modulator. Also, the invention relates to methods of making and using the standard, and kits comprising the standard.

16 Claims, 2 Drawing Sheets

OTHER PUBLICATIONS

Sadar, "Turbidity Science", Technical Information Series-Booklet No. 11, 1998, Hach Company.

"Amco Clear Products for Water Testing and Turbidity", GFS Chemicals, Jul. 17, 2007, http://www.gfschemicals.com/productcatalog/Amco_Clear_Information.asp.

"Determination of Turbidity by Nephelometry", Methods for Chemical Analysis of Water and Wastes, Method 180.1, Revision 2, Cincinnati, Ohio, Aug. 1993.

"NIST-Traceable", Laboratory Network.com, Jul. 7, 2000, http://www.laboratorynetwork.com/Content/news/article.asp.

"Turbidity", Turbidity Measurement 101 Brochure, FTS Forest Technology Systems Ltd., Victoria, British Columbia, Canada.

STABLE TURBIDITY CALIBRATION STANDARDS

CROSS-REFERENCE TO RELATED APPLICATIONS

The present application claims benefit from U.S. Provisional Patent Application No. 60/969,213, filed Aug. 31, 2007, which application is hereby incorporated by reference in its entirety.

The present invention generally relates to stable single layer and multi-layer turbidity calibration standards, methods of making and using the standards, and kits comprising the standards.

BACKGROUND OF THE INVENTION

Turbidimetry is a science of measuring decreased intensity of light caused by scattering or absorption of the light by an inhomogeneous system. The light scattering and absorption can be caused, for example, by an inhomogeneous system comprising solid particles distributed in a liquid, wherein the solid and the liquid have different indices of refraction, or by an inhomogeneous mixture of two liquids having different indices of refraction.

Turbidity is a measurable value for a sample. Turbidity of a sample can be related to an intensity of an incident light and an intensity of a transmitted light (after scattering and assuming there is no absorption of the light) by the following expression:

$$I = I_0 e^{-\tau L}$$

wherein $I_0$ is the intensity of the incident light, I is the intensity of the transmitted light, $\tau$ is turbidity, and L is an optical path length, i.e., a distance through the sample that the light traverses.

Measurements of turbidity are typically reported in units called Nephelometric Turbidity Units (NTU), also called nephelos turbidity units. When suspended formazin is tested in a nephelometer apparatus, the turbidity units are referred to as Formazin Nephelometric Units (FNU). An instrument for measuring water turbidity is called a turbidimeter. Some turbidimeters are called haze meters, which can be used to measure turbidity of gas, including atmospheric gas. Units of turbidity also can be expressed as European Brewery Convention (EBC) units of the International Organization for Standardization (ISO) or Formazin Turbidity Units (FTU) of the American Society of Brewing Chemists (also known as ASBC-FTU). Other units of turbidity are Formazin Attenuation Units (FAU).

Turbidimetry is used in a variety of applications. For quality control or public health purposes, turbidity, including haze, of chemical reactions, formulations, and quality testing samples is monitored using known turbidity assay methods. Turbidity assays measure a degree of "cloudiness," haziness, or opaqueness of a test sample. Turbidity testing is performed with nephelometers, turbidimeters and haze meters in diverse industries such as personal care products, consumer products such as cleaning mixtures, and water and beverage quality testing. Turbidity of test sample aliquots is measured and referenced to turbidity calibration standards to assess progress and quality of process steps or quality testing samples.

Turbidity assay methods and instruments are known. In one type of turbidity assay method, for example, a nephelometer apparatus measures light from a light source beam that is scattered off suspended particles or a discontinuous liquid (e.g., suspended liquid droplets) at 90° from the light source beam. The light source beam typically is in near infrared wavelengths and are selected in order to reduce any potential effects of color, if any, in a test sample.

Robust single layer standards are required for calibrating conventional turbidity measuring instruments, including haze meters. A conventional single layer turbidity calibration standard consists of solid particles suspended in a liquid. An example of such a standard is AMCO Clear® (APS Analytical Standards, Inc., a subsidiary of GFS Chemicals, Inc., Powell, Ohio), which consists of styrene divinylbenzene submicrometer copolymer beads (121 nm average diameter) suspended in an ultra-pure aqueous media. The beads can be suspended in the aqueous media for a period of time due to a phenomenon known as Brownian motion, a random movement of small particles suspended in a liquid or gas medium caused by collisions of the particles with molecules of the medium.

Drawbacks of conventional turbidity standards include settling of suspensions and evaporation and yellowing of liquids upon exposure to turbidity measurement or storage conditions. In addition to these drawbacks, other weaknesses are known. For example, there are physical limitations of Brownian motion. Consequently, standards that rely on Brownian motion to maintain suspension of particles are limited by the size of particles that may be suspended in a liquid. Further, an AMCO standard designed for one turbidimeter cannot be reliably used with a different type of turbidimeter, even if these meters are from a same manufacturer. Also, formazin has been used as a standard, but dilutions of formazin are highly unstable. Further, while a "stabilized formazin" (e.g., STABLCAL™, Hach Company, Loveland, Colo.) is more stable than formazin, preparing stabilized formazin requires strictly following a special mixing protocol. And a refractive index of low level stabilized formazin standards is very different from that of low level formazin standards and from most ultra-pure turbidity water. Differences in refractive indices can lead to very different test results. So, a turbidimeter calibrated with stabilized formazin at low levels cannot be verified with formazin standards. Further, producing standards having stable distributed suspensions of a discontinuous liquid in a different, continuous liquid has been problematic.

Also, temperature-dependent measurements of turbidity such as in studies of properties of polymers (e.g., molecular weight distribution studies) require turbidity calibration standards to work across a wide temperature range from below 0° C. to above 150° C. For example, a polymer sample may be dissolved in a solution at or near a precipitating temperature and then the temperature of a resulting mixture is lowered so that the polymer begins to precipitate out of solution, thereby increasing turbidity of the mixture (see Cantow Manfred J. R., ed. Polymer Fractionation, 1967, Academic Press, pages 191 to 211). Under these conditions, water-based and other liquid-based turbidity calibration standards may freeze, resulting in a turbidity change; concentrate due to evaporation; degrade due to heating; expand volumetrically; or the like.

The above-mentioned drawbacks can preclude an use of a conventional turbidity standard or limit the standard's shelf life to as little as a few days before the standard has to be discarded or remixed, which may or may not restore a suspension to its previous state.

Also, where a test sample has two or more layers, for example an organic layer and an inorganic layer (e.g., an aqueous layer), robust multi-layer turbidity calibration standards that emulate the test sample over a range of layers, concentrations and temperatures are needed to calibrate turbidity measuring instruments. But only single layer turbidity calibration standards have been prepared and used. Turbidity of multilayer test samples conventionally is carried out by dividing the layers from each other, and then separately measuring the turbidity of each of the divided layers. In addition to having the drawbacks mentioned previously for single layer standards, multi-layer turbidity test samples tend to develop a rag layer at an interface between two layers. The rag layer is due to partial mixing of the layers, which then are unusable. Three or more layer standards would compound the rag layer stability problem intrinsic to multi-layer turbidity standards. Historically, multilayer turbidity standards comprised of two or more liquid-based layers were also expected to also develop rag layers, and thus are unknown.

As chemical reaction, formulation, and quality testing samples become more complex, greater numbers of single layer and multi-layer turbidity test samples are needed. Further, globalization of industry research and manufacturing is increasing a need to transfer turbidity calibration protocols from site to site. Stable and reliable single and multi-layer turbidity calibration standards are required for testing increasing numbers of turbidity test samples and for calibrating turbidity measuring instruments at one research site to different such instruments at another research site or manufacturing site.

There is an increasing need in diverse industries for stable single layer and multi-layer turbidity calibration standards to provide reliable reference points in analyses of turbidity of single and multi-layer reaction, formulation, and quality testing samples. The standards could be used for calibration and quality control purposes. Ideally, the standards would resist time- and temperature-dependent changes to turbidity (e.g., due to settling or agglomeration of suspended solids or discontinuous liquids), color (e.g., due to oxidation), composition (e.g., due to reaction), or concentration (due to evaporation or volume expansion upon heating), as well as resist migration of components from layer to layer.

SUMMARY OF THE INVENTION

The present invention generally relates to stable single layer and multi-layer turbidity calibration standards, methods of making and using the standards, and kits comprising the standards. The invention standards are comprised, in part, of light-permeable polymer or interpolymer layers that resist time- and temperature-dependent changes to turbidity, color, composition, and concentration, and migration of components from layer to layer. In some embodiments, at room temperature (e.g., 25° C.), there is no substantial rag layer between any two layers of a multi-layer standard, there are no substantial vacuum or gas pockets in or between layers, and the single layer or each layer of the multi-layers is substantially non-flowable.

A first embodiment of the invention (a first embodiment) is a turbidity calibration standard comprising: a number of from 1 to 5 sequentially-interfaced layers, wherein each layer independently comprises a light-permeable polymer or light-permeable interpolymer; a measured light transmission modulating amount of at least one light transmission modulator, which is distributed in any one or more of the layers; and a light-permeable container, which contains the layers and the at least one light transmission modulator.

Another embodiment is a method of calibrating a turbidity measuring instrument, the method comprising the following steps: (a) providing a turbidity calibration standard of the first embodiment and a turbidity measuring instrument; (b) measuring turbidity of the turbidity calibration standard with the turbidity measuring instrument to produce a reference value of turbidity; (c) at a time after step (a), measuring turbidity of the turbidity calibration standard with the turbidity measuring instrument to produce a test value of turbidity; (d) determining a magnitude of deviation of the test value of turbidity from the reference value of turbidity; (e) adjusting, if necessary, at least one setting of the turbidity measuring instrument based on the determination of step (d); and (f) repeating steps (c) to (e) until the magnitude of deviation is acceptable.

Another embodiment is a method of transferring turbidity calibration from a first turbidity measuring instrument to a second turbidity measuring instrument, the method comprising the following steps: (a) providing a turbidity calibration standard of the first embodiment, a first turbidity measuring instrument, and a second turbidity measuring instrument, wherein the first and second turbidity measuring instruments are different; (b) measuring turbidity of the turbidity calibration standard with the first turbidity measuring instrument to produce a reference value of turbidity; (c) measuring turbidity of the turbidity calibration standard with the second turbidity measuring instrument to produce a test value of turbidity; (d) determining a magnitude of deviation of the test value of turbidity from the reference value of turbidity; (e) adjusting, if necessary, at least one setting of the second turbidity measuring instrument based on the determination of step (d); and (f) repeating steps (c) to (e) until the magnitude of deviation is acceptable.

Another embodiment is a process for preparing a turbidity calibration standard of the first embodiment, the process comprising the following steps: (a) independently providing at least one polymerizable monomer; (b) optionally, independently providing a light transmission modulator, wherein the light transmission modulator is independently selected; (c) if a light transmission modulator is provided in step (b), distributing the light transmission modulator in the at least one polymerizable monomer to give a mixture of the light transmission modulator distributed in the at least one polymerizable monomer; (d) adding the at least one polymerizable monomer of step (a) and, if provided, the light transmission modulator of step (b) or adding the mixture of step (c) to a light-permeable container; (e) polymerizing the at least one polymerizable monomer in the light-permeable container to yield a first layer comprising a first light-permeable polymer or a first light-permeable interpolymer, and, optionally, a light transmission modulator distributed in the first light-permeable polymer or the first light-permeable interpolymer; and (f) repeating steps (a) to (e) from 0 to 4 more times, each time independently selecting at least one polymerizable monomer and, optionally, a light transmission modulator to further yield second to fifth light-permeable layers, respectively; wherein at least one of the first to fifth layers contains a light transmission modulator distributed therein.

Another embodiment is a kit comprising a turbidity calibration standard of the first embodiment; information about a turbidity measurement of the turbidity calibration standard measured with a first turbidity measuring instrument; and instructions for use of the turbidity calibration standard in calibrating the first turbidity measuring instrument or instructions for transferring turbidity calibration from the first turbidity measuring instrument to a second turbidity measuring instrument.

Additional embodiments are described in accompanying drawings and the remainder of the specification.

DETAILED DESCRIPTION OF THE INVENTION

Figure 1:
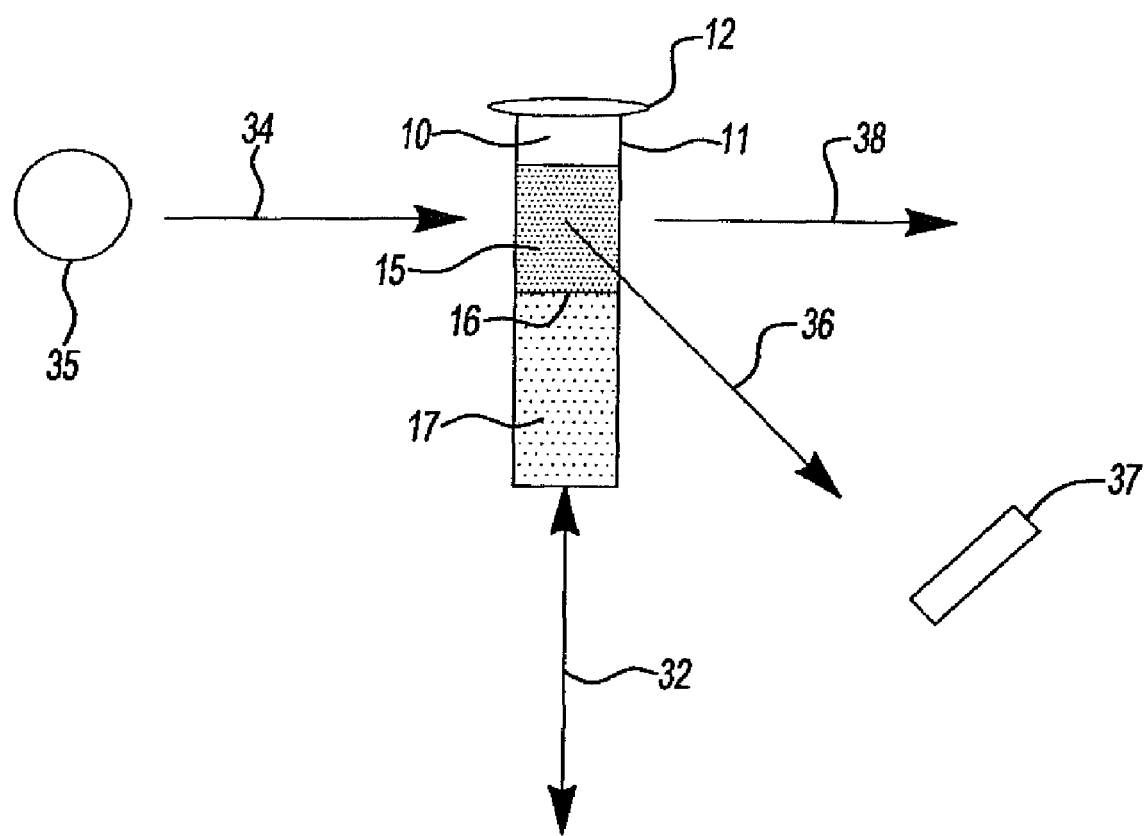
FIG. 1 illustrates an example of a method of scanning a two-layer turbidity calibration standard of the invention with a turbidity measuring instrument.

The present invention is summarized above and further described below. Hereinafter in the description, a light-permeable polymer, light-permeable interpolymer, and the like optionally may be referred to for convenience simply as a polymer, interpolymer, and the like. Below where terms such as "polymer," "interpolymer," and the like are used, it is intended that references are made to a polymer, interpolymer, and the like that is light-permeable, unless it is stated otherwise. Hereinafter, embodiments may be described for convenience using a list format. For example, "[i]n other embodiments, the pigment is a powdered metal carbonate wherein the metal is calcium, cesium, potassium, or sodium." Such embodiments may be claimed using the list format or, optionally, any particular element in a list may be claimed independent of (i.e., without) the other elements being listed.

In describing the present invention, certain abbreviations, phrases, terms, and words are used that are defined here. When interpreting a meaning of an abbreviation, phrase, term, or word, its definition here governs unless, for a particular use, a different meaning is stated elsewhere in this specification or unless a context of the use of the abbreviation, phrase, term, or word clearly indicates a different meaning is intended from the definitions provided here.

Highlighted Abbreviations

FNU—Formazin Nephelometric Units
g—gram(s)
ISO—International Standards Organization
$n_d^{20}$—refractive index of a material, wherein the refractive index is a ratio of the speed of light through a vacuum to a speed of light through the material as measured with a refractometer using sodium D line light at 20° C.
cm—centimeter(s)
mm Hg—millimeter(s) of mercury
nm—nanometer(s)
%—percent
PMMA—polymethylmethacrylate
wt—weight
% wt/wt—percent by weight Articles "a" and "the" refer to singular and plural forms of what is being modified by the articles. For example, "a turbidity measuring instrument" and "the turbidity measuring instrument" include one and more than one turbidity measuring instrument, wherein two or more such instruments may be the same or different type. When used in front of a first member of a list of two or more members, "a" or "the" independently refer to each member in the list. For example, "a powdered aluminum or powdered copper" refers to a powdered aluminum or a powdered copper. The term "or" refers to members in a list either singly or in any combination.

The term "comprising," which is synonymous with the terms "including," "containing," "having," "characterized by," and the like is inclusive or open-ended. Likewise, the term "group of" is also open-ended. These terms do not exclude additional elements, materials, ingredients, or method steps, including unrecited ones, even if the additional elements, materials, ingredients, or method steps are present in major amounts. When the term "comprising" is used as a transition from a claim's preamble to the claim's body (i.e., as a transitional term), the entire claim is open-ended.

The phrases "consisting of" or "group consisting of" are closed terms. These phrases exclude any element, step, or ingredient not specified. When the phrase "consisting of" is used as a transitional phrase in a claim, the phrase closes the claim to the inclusion of materials, elements, or steps that are not specifically recited in the claim except for impurities ordinarily associated therewith and materials, elements or steps that are unrelated to the claimed invention. When the phrase "consisting of" is used in a clause of the body of the claim rather than immediately following the preamble, it limits only the element, step, material or the like set forth in that clause and other elements, materials, or steps outside of the clause are not excluded from the claim. The present invention also includes embodiments written by modifying the "comprising" embodiments described elsewhere herein by replacing the transitional term "comprising" with the transitional phrase "consisting of."

The phrase "consisting essentially of" may be used in a claim's preamble to limit the scope of the claim to the specified materials, elements, or steps and those that do not materially affect the basic and novel characteristic or characteristics of the claimed invention. Referring to preambles, a "consisting essentially of" claim occupies a middle ground between closed claims that are written in "consisting of" format and fully open claims that are drafted in a "comprising" format. The present invention also includes embodiments written by modifying the "comprising" embodiments described elsewhere herein by replacing the transitional term "comprising" with the transitional phrase "consisting essentially of."

A single or multi-layer turbidity calibration standard of the invention is frequently described herein using comprising language. Nevertheless, the invention excludes the standard from further comprising a liquid layer (i.e., a layer consisting essentially of: a liquid monomer(s), water, an aqueous solution, or the like).

The phrase "adjusting, if necessary, at least one setting of the turbidity measuring instrument" refers to manipulating a variable of a turbidity measuring instrument. In some embodiments, the turbidity measuring instrument is comprised of a light detector (e.g., a digital camera) that may or may not be in communication with a light source. In other embodiments, the light detector and light source are in communication with each other. In any event, if needed or desired, adjusting is performed by, for example, varying input light intensity, detector angle (between transmitted (e.g., scattered) light vector and incident light vector), detector sensitivity (to light), distance between input light source and test sample, and the like in an attempt to reduce or minimize a magnitude of deviation of a test turbidity value from a reference turbidity value or to eliminate the deviation. If a "calibration factor" can be used to calibrate data from an instrument without adjusting any settings, then the adjusting step is not necessary. Even if adjusting a setting is not necessary to calibrate data, however, the settings can still be adjusted if desired to reduce the magnitude of deviation.

The term "calibrating" means to standardize by determining a magnitude of deviation of a test turbidity value from a reference turbidity value and, if the magnitude of deviation is not acceptable (i.e., if it is too large to allow a calibration required by the circumstances of a particular test sample), adjusting measurement variables until the magnitude of deviation is acceptable. In some embodiments, measurement variables are not adjusted to attenuate the magnitude of deviation, but the magnitude of deviation is used to determine a calibration factor for correcting turbidity values of test samples for magnitude of deviation in order to generate substantially comparable data. In other embodiments, measurement variables are adjusted. Measurement variables include input light intensity, detector sensitivity, detection angle, and distance between input light source and test sample. Measurement variables also include cleanliness of a sample container, protection of a detector from stray light, and the like. Ideally, adjusting measurement variables reduces or minimizes the magnitude of deviation, or eliminates the deviation. If the magnitude of deviation is eliminated, use of a calibration factor to correct turbidity values of test samples for magnitude of deviation is not necessary. If the magnitude of deviation is reduced but not eliminated, the calibration factor may or may not be used, depending on the circumstances. In any event, a "magnitude of deviation is acceptable" if a test value can be calibrated to a reference value of turbidity with or without a calibration factor. Calibration factors include mathematical operations such as those described by algebraic equations or factor numbers that convert a test measurement of turbidity to a reference value of turbidity. When a calibration factor is used to calibrate two or more test measurements of turbidity to range of common reference values, turbidity measurements taken at different times or with different instruments can be reliably compared, even statistically compared.

For purposes of the invention, any method is acceptable for "determining a magnitude of deviation" between two turbidity values. One such method is simply to calculate a difference between the two values by subtracting one value from the other value (e.g., 10 FNU−5 FNU=5 FNU=a magnitude of deviation). The term "measuring turbidity" means experimentally producing a value of turbidity. When magnitude of deviation from a turbidity calibration standard is being determined, substantially a same protocol for measuring a reference value and a test value of turbidity ideally should be followed.

The term "sequentially-interfaced layers" and "layers" are synonymous and mean that a number of layers are connected in series and each layer is in physical contact with its immediate neighbor(s). In such layers, there is no substantial gap (e.g., air) between a top face of a bottom of a light-permeable container and a bottom face of a bottom layer (with or without a light transmission modulator suspended therein) or between opposing faces of any two adjacent layers when the number of layers is more than one. For example, if multiple layers are sequentially interfaced in a vertical orientation in a container having a bottom and sides, which may be circular, a bottom face of a bottom layer is in substantial contact with a top face of the bottom of a container, a top face of the bottom layer is in substantial contact with a bottom face of a second layer, a top face of the second layer is in substantial contact with a bottom face of a third layer, and so on up.

An interface between any two layers may or may not take a form of a meniscus, which, if present, may or may not be detectable with a naked eye. A shape of the meniscus may be concave or convex. Similarly, a top face of a top layer of a multi-layer standard or a top face of a single layer standard may or may not take a form of a meniscus. The shape of the meniscus may be concave or convex.

In some embodiments, the standard consists essentially of a single layer (i.e., 1 layer) standard. In other embodiments, the standard consists essentially of a multi-layer standard having a number N of layers. In some embodiments, N is an integer 4 or 5. In other embodiments, N is 1 or 2. In other embodiments, N is 3; N is 2; or N is 1.

Every variable aspect of a single layer standard and of each layer of a multilayer standard is independently chosen. For example, each layer of a multilayer standard may be comprised of a same or different polymer or interpolymer. Each layer of a multilayer standard may contain a same or different of at least one light transmission modulator, or no light transmission modulator. In a multilayer standard wherein two or more layers independently contain at least one light transmission modulator, each layer may contain a same or a different light-modulating amount of the at least one light transmission modulator. Each layer of any standard may be a same or a different height or color. These and other variables of a standard may be readily chosen in order to emulate a particular type of turbidity test sample being analyzed.

Phrases in a general form "A and, optionally, B or C" means A and B, A and C, or A, but not B and not C (i.e., the form does not require that the B or the C be included with the A). In some cases, the phase "if present" may be used in place of the term "optionally." (The letters "A," "B," and "C," are used for convenience of description purposes only.)

The term "distributing" means mixing, dispersing, suspending, or broadcasting solid domain particles in a liquid monomer or a mixture of two or more liquid monomers or mixing, dispersing, suspending, broadcasting, or emulsifying liquid domain groups in a liquid monomer or a mixture of two or more liquid monomers, wherein the monomer or two or more monomers may be in an act of polymerizing during the distribution. A distributing step may be carried out in a light-permeable container or the step may be carried out in a different container, including aluminum weight pans and the like, and then later a resulting mixture may be added to the light-permeable container after the distributing step is complete.

The term "distributed" in the phrase "distributed in any of the layers" means dispersed, suspended, emulsed, or otherwise broadcast throughout any one or more of the layers. In some embodiments, a distribution is substantially uniform or completely uniform throughout. In other embodiments, the distribution is in a form of a concentration gradient. In other embodiments, the distribution is in the form of a concentration gradient from lowest concentration at a top-most portion of the layer to highest concentration at a bottom-most portion of the layer. In other embodiments, the distribution is in the form of a concentration gradient from highest concentration at a top-most portion of the layer to lowest concentration at a bottom-most portion of the layer (e.g., when a solid domain has a density that is lower than a density of the polymer or interpolymer comprising the layer).

The terms "independent," "independently," and the like refer to selecting one option without regard for, or irrespective of, what has been selected for another option, or making one choice without regard for, or irrespective of, what has been made for another choice. For example, regarding the phrase "independently providing at least one polymerizable monomer," in some embodiments one polymerizable monomer is provided to form a particular light-permeable layer. In other embodiments two or more polymerizable monomers are provided to form a particular light-permeable layer. In the embodiments where two or more polymerizable monomers are provided to form a particular light-permeable layer, a choice of monomer for one of the two or more polymerizable monomers is independent of a choice of monomer of every other monomer of the two or more polymerizable monomers.

The term "measured light transmission modulating amount" relates to any way of referencing an amount of a light transmission modulator in a given layer to the amount of the layer or to a level of turbidity of the layer. Any way of describing the light transmission modulating amount is useful in the invention. Such ways include expressing the amount as a weight/weight percent; it is known that there is more than one way of calculating a weight/weight percent. Alternatively, a measured light transmission modulating amount of a light transmission modulator in a layer may be described as a known weight in grams of a light transmission modulator that is distributed in a known weight in grams of a polymer or interpolymer that comprises the layer. In any event, a measured light transmission modulating amount is effective for changing a reading of a nephelometer by at least 0.002 FNU using protocol ISO 7027, which is described below. Examples include a single layer turbidity standard comprising 0.101% weight/weight of talc distributed in a light-permeable silicone-based polymer and contained in a transparent glass vial and a single layer turbidity standard comprising 0.10015 g of talc distributed in 10.34 g of a light-permeable silicone-based polymer and contained in a transparent glass vial.

A measured light transmission modulating amount of a light transmission modulator in a layer may be described in terms of a known turbidity value, which may be expressed as a unit of turbidity described previously, a grayscale value, and the like. An example is a 100 FNU single layer turbidity standard comprising talc distributed in a light-permeable silicone-based polymer and contained in a transparent glass vial.

In some embodiments, each light transmission modulator is present in an amount that is greater than 0.002 FNU, as determined using ISO 7027. In other embodiments, a light transmission modulator is present in an amount that is from 0.002 FNU to one hundred thousand FNU (100,000 FNU). In other embodiments, a light transmission modulator is present in an amount that is: greater than 0.005 FNU; from 0.01 FNU to 100,000 FNU; from 0.1 FNU to 50,000 FNU; from 0.1 FNU to 10,000 FNU; or from 0.1 FNU to 5,000 FNU.

When two or more different light transmission modulators are present in the layer, there is an independent measured light transmission modulating amount of each modulator. When a same light transmission modulator is distributed in two or more layers of a multi-layer standard of the invention, there is an independent measured light transmission modulating amount of the light transmission modulator in each layer in which the light transmission modulator is distributed.

For purposes of determining whether a turbidity sample is within or outside a scope of the present invention, a light transmission modulating amount of a light transmission modulator in a layer is measured using a standard protocol ISO 7027, which is referenced below. For purposes of preparing a turbidity calibration standard of the invention, however, other methods of measuring turbidity may be used. Examples of the other methods include measuring turbidity as grayscale values with a digital camera and image processing software or measuring turbidity in Nephelometric Turbidity Units (NTU), also called nephelos turbidity units with a turbidimeter following a standard EPA 180.1 method described in Methods for Chemical Analysis of Water and Wastes, Method 180.1, Determination of Turbidity by Nephelometry, Revison 2, Cincinnati, Ohio, August 1993. This method specifies a tungsten lamp with a color temperature of 2,200 to 3,000 degrees Kelvin (2K) and turbidity is recorded as NTU. (The United States Environmental Protection Agency (EPA) requires turbidity values not to exceed 0.3 NTU for surface source drinking water as measured using EPA 180.1.)

Expressing a measured light transmission modulating amount in terms of weight percent rather than FNU is useful for preparing duplicate standards according to a recipe that calls for a specified weight of a light transmission modulator to be distributed in a specified weight of a polymer or interpolymer. In certain embodiments, the amount of a light transmission modulator is from greater than 0 percent (%) by weight to about 10% by weight (i.e., >0% wt/wt to about 10% wt/wt) of the light transmission modulator to weight of the polymer or interpolymer that comprises the layer. In other embodiments, the amount is from >0% wt/wt to about 1.0% wt/wt; >0% wt/wt to about 0.10% wt/wt; from 0.0001% wt/wt to 10% wt/wt; from 0.0001% wt/wt to 1.0% wt/wt; or from 0.0001% wt/wt to 0.10% wt/wt. For low % wt/wt values (i.e., those just above 0% wt/wt) of any particular light transmission modulator, if such an amount of the light transmission modulator is not effective for changing a reading of a nephelometer by at least 0.002 FNU using ISO 7027, the amount is not light-transmission modulating for purposes of the invention.

The term "light transmission modulator" means a solid domain or liquid domain as defined herein. Theoretically, but without being bound by a theory, when distributed in a polymer or interpolymer, the light transmission modulator affects the transmission of light through the polymer or interpolymer by scattering or scattering and absorbing wavelengths of light in an ultraviolet (UV), infrared (IR), or visible (VIS) region of a light spectrum, or a combination thereof. In some embodiments, the light useful in measuring turbidity comprises a portion of the IR region of the light spectrum. In such embodiments, a conventional nephelometer may be used to measure turbidity. In other embodiments, the light useful in measuring turbidity comprises a portion of the VIS region of the light spectrum. In such other embodiments, a digital camera in communication with image processing software and a display or a conventional VIS light detector may be used to measure turbidity. In still other embodiments, the light useful in measuring turbidity comprises a portion of the UV region of the light spectrum. In such still other embodiments, a nephelometer adapted with a UV light detector may be used to measure turbidity. The IR, VIS, and UV detectors include static wavelength and variable wavelength (e.g., scanning) detectors.

In the invention, any given polymer or interpolymer layer may or may not contain a light transmission modulator distributed therein. When more than one light transmission modulator is present in a turbidity calibration standard of the invention, each light transmission modulator is independently selected. When, as in some embodiments, there is more than one layer, each layer independently may or may not have a light transmission modulator distributed therein. In some embodiments, there is only one light transmission modulator in any given layer. In some embodiments, two or more different light transmission modulators are distributed in any given layer. There may be two or more different solid domains in a turbidity calibration standard of the invention, two or more liquid domains in a turbidity calibration standard of the invention, or any combination thereof in a turbidity calibration standard of the invention. There may be two or more different solid domains in a given layer, two or more liquid domains in a given layer, or any combination thereof in a given layer.

At room temperature, some interpolymers (e.g., block interpolymers such as block copolymers) consist essentially of crystalline solid regions distributed in amorphous solid regions (or first amorphous solid regions distributed in second amorphous regions). Upon heating to a temperature above a glass transition temperature ($T_g$) but below a crystalline solid melt temperature ($T_m$) (or below a melt temperature of the first amorphous regions), the amorphous solid regions of the interpolymer will melt or liquefy while the crystalline solid regions (or the first amorphous regions) will remain solid. Such interpolymers may give a false appearance of being comprised of independent particulate solids distributed in a polymer or interpolymer or distributed in a melted polymer or interpolymer, respectively. The invention excludes these crystalline solid regions and first amorphous regions from being a light transmission modulator.

A turbidity calibration standard of the invention may be at almost any temperature when it is used in an invention method of calibrating a turbidity measuring instrument. The temperature of the standard will be appropriate under circumstances desirable for measuring turbidity a particular test sample. The temperature of the test sample may be at, below, or above room temperature when turbidity of the test sample is measured. So, it may be desirable for the temperature of the standard to be at, below, or above room temperature when turbidity of the standard is measured. In some embodiments, the temperature of the standard when the standard is used in an invention method of calibrating a turbidity measuring instrument is room temperature (i.e., from 20° C. to 30° C., e.g., 25° C.). In other embodiments, the temperature is above room temperature (i.e., above 30° C.). In such embodiments, a layer or layers may be in a melt state. In still other embodiments, the temperature is below room temperature (i.e., below 20° C.).

In some embodiments, a light transmission modulator, when compared to a polymer or interpolymer in which the light transmission modulator is distributed, has a relative density of from about 0.5 to about 1.5 (i.e., a density of the light transmission modulator divided by a density of the polymer or interpolymer is from about 0.5 to about 1.5). In other embodiments, the light transmission modulator, when compared to the polymer or interpolymer in which the light transmission modulator is distributed, has a relative density of from about 0.75 to about 1.25; from about 0.85 to about 1.15; or from about 0.93 to about 1.07.

In some embodiments, a refractive index of a light transmission modulator is higher than a refractive index of a polymer or interpolymer comprising the layer by at least 0.010 (i.e., a difference in refractive indices ("refractive index difference"), which equals the refractive index ($n_d^{20}$) of the light transmission modulator minus the $n_d^{20}$ of the polymer or interpolymer, is greater than or equal to 0.010). In other embodiments, the refractive index difference is: at least 0.050; at least 0.10; or at least 0.50. In some embodiments, the refractive index of a light transmission modulator will not be higher than the refractive index of a polymer or interpolymer comprising the layer by more than 4.0. In other embodiments, the refractive index of a light transmission modulator will not be higher than the refractive index of a polymer or interpolymer comprising the layer by: more than 3.0; more than 2.0; or more than 1.0.

In some embodiments, a polymer or interpolymer layer contains a liquid domain distributed therein, with or without a solid domain also being distributed therein. For purposes of the invention, the term "liquid domain" refers to a flowable material that can be divided into discontinuous groups (e.g., discontinuous droplets (i.e., o/o, wherein each "o" is an independent droplet separated by a barrier of polymer or interpolymer "/"), a mix of droplets and agglomerated groups (i.e., a mix of o/o and oo), and the like. In some embodiments, an average diameter of the groups is greater than 1 micrometer. In other embodiments, the average diameter or the groups is 1 micrometer or less (micro-groups). A liquid domain modulates transmission of light through a polymer or interpolymer layer containing the liquid domain distributed therein when the layer is exposed to a light source useful in turbidity measurements and a refractive index of the liquid is higher than a refractive index of the polymer or interpolymer.

To prepare a light permeable polymer or interpolymer layer having a liquid domain distributed as groups therein, a liquid typically is mixed (e.g., by agitation such as shaking, microwave agitation, mechanical stirring, vibration, and the like) with at least one polymerizable monomer and, if necessary, mixing continues for a sufficient period of time while the monomer(s) polymerizes. Then the liquid domain is trapped as distributed groups in the polymer or interpolymer.

Any average size of groups comprising a distributed liquid domain will work in the invention provided liquid domain is able to be distributed in a layer of polymer or interpolymer. In some embodiments, a liquid domain is distributed as groups having an average diameter of less than 10 micrometers. In other embodiments, the groups have an average diameter of: less than 5 micrometers; less than 2 micrometers; less than 1 micrometer; or from about 0.1 micrometer to about 1 micrometer.

A liquid domain is not the same as an unpolymerized monomer or monomers that may comprise a polymer or interpolymer.

In some embodiments, a liquid domain modulates transmission of light by scattering the light. In still other embodiments, the liquid domain scatters and absorbs the light.

In other embodiments, a liquid domain comprises water, an aqueous solution, olive oil, soybean oil, safflower oil, fish oil, medium-chain triglyceride oil, milk fats, a silicone-based oil, gasoline, motor oil, diesel fuel, kerosene, crude oil, hydraulic oil, lubricant oil, or a solution comprising such a liquid domain.

In some embodiments, a polymer or interpolymer layer contains a solid domain distributed therein, with or without a liquid domain. For purposes of the invention, the term "solid domain" refers to a powdered solid material, micrometer beads, nano-scale tubes, and the like. For purposes of the present invention, the term "powdered" refers to a physical form of a material. A powdered material includes a particulate or finely divided material. A powdered material has an average particle size as disclosed herein for it. A solid domain modulates transmission of light through a polymer or interpolymer layer containing the solid domain distributed therein when the layer is exposed to a light source useful in turbidity measurements. When the solid domain in a particular layer is comprised of a polymer or interpolymer, the polymer of interpolymer comprising the solid domain is different than the polymer or interpolymer comprising the particular layer. A solid domain typically is present in a polymerizable monomer or monomers prior to or added during polymerizing a monomer or monomers to prepare a light permeable polymer or interpolymer.

In some embodiments, a solid domain comprises a pigment, carbon nanotube, powdered polymer, powdered interpolymer, polymer bead, or interpolymer bead.

Any average solid domain particle size will work for a solid domain provided the solid domain is able to be distributed in a layer or layers. In some embodiments, the average size of the particles comprising the solid domain is in a range of from about 0.1 micrometer to about 50 micrometers. In other embodiments, the average size of the solid domain particles is in a range of: from about 0.75 micrometer to about 50 micrometers; from about 0.75 micrometer to about 25 micrometers; or from about 0.75 micrometer to about 10 micrometers. In other embodiments, the average size of the solid domain particles is from about 1.0 micrometer to about 10 micrometers.

Any particle size distribution range will work for the solid domain provided the solid domain is able to be distributed in the layer or layers. In some embodiments, the particle size distribution range for 95% or the material is from about 0.1 times the average particle size (APS) to about 10 times the APS. In other embodiments, the particle size distribution range for 95% or the material is: from about 0.2 times to about 5 times the APS or from about 0.5 times to about 2 times the APS.

In some embodiments, a solid domain modulates transmission of light useful in a turbidity measurement assay by scattering the light. In other embodiments, the solid domain scatters, and absorbs the light.

Solid domains may be white or colored, which includes black. Examples of white solid domains include talc, silica spheres, and powdered titanium dioxide. Examples of colored solid domains include powdered carbon black, powdered iron (II) oxide, powdered iron (III) oxide, powdered cadmium sulfide, powdered ferric-ferrocyanide, and the like.

A solid domain is substantially insoluble (i.e., very slightly soluble or <5% weight dissolved solid domain/total solid domain weight) or completely insoluble (i.e., 0% wt/wt) in a polymer or interpolymer.

In some embodiments, solid domains are inorganic in nature. In other embodiments, solid domains are organic in nature.

In some embodiments, a solid domain is a "pigment." A pigment includes a powdered ferric-ferrocyanide, a powdered cadmium sulfide, a powdered metal, a powdered metal carbonate, a powdered metal oxide, and a powdered silicate. In other embodiments, the pigment is comprised of powdered carbon black.

In other embodiments, a pigment is a powdered metal oxide that is a powdered: aluminum(III) oxide, cadmium(II) oxide, chromium(III) oxide, chromium(IV) oxide, cobalt(II) oxide, copper(I) oxide, copper(II) oxide, iron(II) oxide, iron (III) oxide, lead(II) oxide, manganese(IV) oxide, nickel(II) oxide, palladium(II) oxide, rhodium(III) oxide, ruthenium (IV) oxide, silicon dioxide, silver(I) oxide, silver(II) oxide, tin(II) oxide, tin dioxide, titanium(II)oxide, titanium(III) oxide, titanium dioxide, tungsten(III) oxide, and zirconium dioxide. In other embodiments, the pigment is aluminum(III) oxide, chromium(III) oxide, chromium(IV) oxide, iron(II) oxide, iron(III) oxide, silicon oxide that is a fumed silica, or titanium dioxide.

In some embodiments, a pigment is a powdered metal silicate wherein the metal is: aluminum, barium, beryllium, calcium, iron, magnesium, manganese, potassium, sodium, or zirconium. In other embodiments, the pigment is a powdered magnesium silicate. In other embodiments, the pigment is powdered talc. The term "talc" means a mineral having the molecular formula $Mg_3Si_4O_{10}(OH)_2$. Talcum powder is a finely divided form of talc.

In some embodiments, a pigment is powdered carbon black. In some embodiments, a pigment is powdered ferric-ferrocyanide. In some embodiments, a pigment is powdered cadmium sulfide.

In other embodiments, a pigment is a powdered metal. In other embodiments, the pigment is a powdered metal that is a powdered: aluminum, copper, gold, iron, lead, nickel, palladium, platinum, silicon, silver, tin, titanium, tungsten, or zinc.

In some embodiments, a pigment is a powdered metal carbonate. In other embodiments, the pigment is a powdered metal carbonate wherein the metal is calcium, cesium, potassium, or sodium.

In some embodiments, a solid domain is comprised of powdered or beaded polymer or interpolymer, including a standard polymer and interpolymer used in latexes of polymers and interpolymers. In other embodiments, the solid domain is comprised of polymer beads. In other embodiments, the solid domain is comprised of interpolymer beads. In other embodiments, the solid domain is comprised of copolymer or terpolymer beads. In other embodiments, the solid domain is comprised of powdered acrylate polymer, powdered styrene butadiene copolymer, styrene divinylbenzene copolymer beads or sub-micrometer styrene divinylbenzene copolymer beads. In other embodiments, the solid domain is comprised of styrene divinylbenzene copolymer beads or sub-micrometer styrene divinylbenzene copolymer beads.

The term "polymer bead" or "interpolymer bead" refers to an approximately spherical polymer or interpolymer particle. Polymer and interpolymer beads may be prepared by conventional droplet or suspension polymerization processes.

In some embodiments, a solid domain is comprised of carbon nanotubes. The term "carbon nanotube" refers to an allotrope of carbon having a structure that is cylindrical and, typically, a diameter of about one nanometer. Carbon nanotubes also include partially fractured (e.g., as a result of applying a "powdering" mechanical force) mixtures thereof. An average aspect ratio (i.e., length-to-diameter ratio) of the carbon nanotubes may be any ratio provided the nanotubes are able to be suspended in a polymer or interpolymer. In some embodiments, the length-to-diameter ratio (e.g., length in nanometers divided by diameter in nanometers) is greater than 10,000.

In some embodiments, each light transmission modulator comprises a solid domain. In other embodiments, each light transmission modulator consists essentially of a solid domain. In such other embodiments, what is meant by "consisting essentially of" is that a liquid domain may be present or not, but if it is present, it is present in a measured light transmission modulating amount of the liquid domain that is lower than a measured light transmission modulating amount of the solid domain. In other embodiments, the liquid domain, if present, is present in an amount less than 0.10% weight or less than 0.05% weight of the liquid domain to weight of a layer containing the liquid domain. In other embodiments, no liquid domain is present.

In some embodiments, each one of a light transmission modulator comprises a liquid domain. In other embodiments, each light transmission modulator consists essentially of a liquid domain. In such other embodiments, what is meant by "consisting essentially of" is that a solid domain may be present or not, but if it is present, it is present in a measured light transmission modulating amount of the solid domain that is lower than a measured light transmission modulating amount of the liquid domain. In other embodiments, no solid domain is present.

The term "light-permeable container" is synonymous with the terms "container" and "transparent container" and means a vessel that is substantially translucent (i.e., substantially clear or transparent). A light-permeable container is not comprised of a polymer or interpolymer. In some embodiments, the vessel is substantially colorless. In other embodiments, the vessel is colored (e.g., tinted glass). The container may be sealed (e.g., capped vial or a hermetically annealed glass vial) or unsealed, gas permeable or substantially gas impermeable.

The container may be under any atmosphere. In some embodiments, the atmosphere is comprised of ambient air. In other embodiments, the atmosphere consists essentially of an inert atmosphere such as nitrogen, argon, helium, and the like.

A light-permeable container includes a cell, cuvette, test tube, vial, well such as a well in a multi-well, high throughput assay plate (e.g., 96-well titer plate), and the like. In some embodiments, the container is dimensioned as a well in a multi-well parallel turbidity measurement plate. In other embodiments, a multi-container parallel turbidity assay method uses a number of vials organized in a multi-holed vial holder such as a block capable of holding from 2 to 100 vials. In other embodiments, the multi-container parallel turbidity assay method uses a carousel containing vials or other container and accessible by a container transfer robotic device. Such devices are commercially available.

Without being held to a theory, due to recognized glass-like or solid-like properties of polymers and interpolymers, a turbidity calibration standard of the invention may be oriented in space relative to the earth in any orientation when being measured (i.e., assayed) in a turbidity measuring instrument. In some embodiments, for example, turbidity of the standard is measured with the standard disposed in a vertical orientation. In other embodiments, the standard is disposed in a horizontal orientation (e.g., in assays using light-permeable 96-well titer plates). In still other embodiments, the standard may be conveniently disposed in an orientation between vertical and horizontal.

In some embodiments, a light-permeable container is comprised of glass. In other embodiments, the glass is PYREX® (Corning Inc., Corning, N.Y., United States of America (USA)) glass ($n_d^{20}$ 1.474); crown—common glass ($n_d^{20}$ 1.52); or fused silica glass ($n_d^{20}$ 1.459). In other embodiments, the container is comprised of LUCITE® (Lucite International, Inc., Cordova, Tenn., USA) ($n_d^{20}$ 1.495); PLEXIGLAS® (Rohm & Haas Company, Philadelphia, Pa., USA) ($n_d^{20}$ 1.488); polycarbonate; polymethylmethacrylate (PMMA), polystyrene; polystyrene-acrylonitrile (SAN), or a like substantially transparent polymer or interpolymer ($n_d^{20}$ typically from 1.460 to 1.55).

The term "light-permeable polymer or light-permeable interpolymer" is synonymous with "light-permeable polymer or interpolymer" and "polymer or interpolymer" and means a polymer or interpolymer that is substantially translucent (i.e., substantially transparent). Physical stresses, changes in temperature, or other conditions may cause small gas or vacuum pockets to form in the polymer or interpolymer due to small gaps forming between the layers or within a layer. These gas or vacuum pockets do not materially affect a use of an invention turbidity calibration standard and a polymer or an interpolymer with such gas or vacuum pockets is part of the invention.

In some process embodiments, a polymer or interpolymer is further processed (e.g., by hydrogenation), for example, if necessary to become light permeable or substantially colorless.

In some embodiments, a light permeable polymer or interpolymer is substantially colorless. In other embodiments, the polymer or interpolymer is colored.

In some embodiments, a polymer or interpolymer is substantially transparent, i.e., has an FNU of less than 5.1, as determined using ISO 7027. In other embodiments, the FNU is: less than 3.1; less than 1.1; or less than 0.6, as determined using ISO 7027.

In some embodiments, a polymer or interpolymer has a refractive index $n_d^{20}$ within about 0.5 of a refractive index of a container that contains the polymer or interpolymer. In other embodiments, the polymer or interpolymer has a refractive index $n_d^{20}$ of: within about 0.2; within about 0.1; or within about 0.05 of the refractive index of the container that contains the polymer or interpolymer.

In some embodiments, a layer comprises a polymer. The polymer may be any substantially transparent polymer. In some embodiments, the polymer comprises a light-permeable: acrylic polymer, elastomer polymer, epoxy polymer, high density polyethylene, polycarbonate, polyester, polymethylmethacrylate (PMMA), polystyrene, polyurethane, polyvinylchloride, polysiloxane polymer, or silicone polymer. In some embodiments, the polymer comprises a light-permeable silicone polymer.

In some embodiments, a layer comprises a interpolymer, which refers to a mixed polymer comprised of two or more interpolymerized monomers (i.e., two or more monomers are polymerized together such that covalent bonds are formed between the resulting polymers, which comprise segments of the interpolymer). In other embodiments, the interpolymer is comprised of 2, 3, or 4 interpolymerized different monomers. In other embodiments, the interpolymer is a terpolymer, which is comprised of three interpolymerized different monomers. In other embodiments, the interpolymer is a copolymer, which is comprised of two interpolymerized different monomers. The interpolymer may be any substantially transparent interpolymer. In some embodiments, a layer comprises a copolymer. In other embodiments, the copolymer comprises a light-permeable styrene-methylmethacrylate copolymer or light-permeable styrene-acrylonitrile copolymer.

In some embodiments, a layer comprises a terpolymer. In other embodiments, the terpolymer comprises a light-permeable ethylene propylene diene terpolymer.

In other embodiments, single layer or each layer of a multilayer standard is comprised of a light-permeable silicone-based polymer.

Polymers and interpolymers useful in the invention may be prepared using conventional polymerization processes, including free radical polymerization, addition polymerization, anionic polymerization, ring opening polymerization, metathesis polymerization, and condensation or step growth polymerization. Generally, the polymers and interpolymers are prepared by polymerizing one monomer or two or more different monomers, respectively. Polymerizing two or more monomers may also be referred to as copolymerizing. The monomers ideally are liquids at a temperature at which they are polymerized. Examples of suitable monomers and details regarding such processes are found in "Polymer Handbook", 4th Ed, Brandrup, Immergut, and Grulke, Eds., Wiley, 1999; and "Copolymerization", G. E. Ham, Ed., *High Polymers*, Vol. XVIII, Interscience, 1964. Examples of substantially transparent copolymer compositions are also found in U.S. Pat. Nos. 7,217,763 B2; 5,665,800; 5,324,802; 5,278,272; 5,272,236; 3,113,114; and 2,471,959. Any unsaturated polymers or interpolymers made by polymerization processes described below or referenced above can be partially or completely hydrogenated to reduce of a level of any unsaturation, including selectively eliminating terminal unsaturation, if desired. One or more olefin monomers, or one or more α-olefin monomers, and a diene, suitably employing, for example, a Ziegler/Natta, metallocene, or other coordination polymerization catalyst, may be used to prepare polymers and interpolymers by addition polymerization. Examples of metallocene polymers or interpolymers useful in the invention include those that are commercially available under trade names such as AFFINITY®, ENGAGE®, or INSITE® (all of The Dow Chemical Company, Midland, Mich., USA); see U.S. Pat. Nos. 5,272,236; 5,278,272; and 5,665,800. Further examples of metallocene polymers or interpolymers useful in the invention include those that are commercially available under trade name EXACT® (Exxon Mobil Corporation, Irving, Tex., USA). What is meant by the term "Ziegler/Natta polymerization catalyst" is a catalyst composition suited for polymerization of olefins comprising an organometallic compound comprised of a metal from groups 2, 12 or 13 of the Periodic Table of the Elements in combination with at least one other compound, especially a halide, oxide or oxyhalide, of a metal selected from groups 4, 5 or 6 of the Periodic Table of the Elements.

The term "polymerizing" means allowing one monomer to polymerize to form a homopolymer, allowing two or more monomers to interpolymerize to form an interpolymer (e.g., two monomers to copolymerize to form a copolymer and three monomers to terpolymerize to form a terpolymer) or, in a case of epoxies, certain elastomers, and the like, allowing an epoxy or an elastomer such as a silicone-based elastomer to cure. Conventional polymerization conditions may be used to prepare a polymer or interpolymer.

General examples of monomers that are useful for preparing a polymer or interpolymer are:

A. Free Radical Polymerization aliphatic and aromatic α-olefins and substituted olefins, conjugated and non-conjugated dienes, and cyclic olefins and polyolefins; and ethylene, propylene, 1-butene, 1-hexene, 1-octene, 4-methyl-1-pentene, acrylonitrile, methylmethacrylate, butylacrylate, styrene, vinylcyclohexane, α-methylstyrene, p-vinyltoluene, vinyl chloride, vinylidene chloride, vinylidene fluoride, tetrafluoroethylene, 1,3-butadiene, isoprene, 2,3-dimethyl-1,3-butadiene, 1,3-pentadiene, 1,3-hexadiene, 1,4-hexadiene, 1,5-hexadiene, 2,4-hexadiene, 2-methyl-3-ethyl-1,3-butadiene, 3-methyl-1,3-pentadiene, 2-methyl-3-ethyl-1,3-pentadiene, 2-ethyl-1,3-pentadiene, 3-methyl-1,3-heptadiene, 3-octadiene, 3-butyl-1,3-octadiene, 3,4-dimethyl-1,3-hexadiene, 3-n-propyl-1,3-pentadiene, 4,5-diethyl-1,3-octadiene, 2-phenyl-1,3-butadiene, 2,3-diethyl-1,3-butadiene, 2,3-di-n-propyl-1,3-butadiene, 2-methyl-3-isopropyl-1,3-butadiene, chloroprene, fluoroprene, 2-methoxy-1,3-butadiene, 2-ethoxy-3-ethyl-1,3-butadiene, 2-ethoxy-3-methyl-1,3-hexadiene, decadiene, divinylbenzene, cyclohexene, vinylcyclohexene, benzocyclobutene, norbornene, norbornadiene, dicyclopentadiene, ethylidene norbornene and mixtures thereof;

B. Addition Polymerization aliphatic and aromatic α-olefins and substituted olefins, conjugated and non-conjugated dienes, and cyclic olefins and polyolefins; and ethylene, propylene, 1-butene, 1-hexene, 1-octene, 4-methyl-1-pentene, acrylonitrile, methylmethacrylate, butylacrylate, styrene, vinylcyclohexane, α-methylstyrene, p-vinyltoluene, 1,3-butadiene, isoprene, 2,3-dimethyl-1,3-butadiene, 1,3-pentadiene, 1,3-hexadiene, 1,4-hexadiene, 1,5-hexadiene, 2,4-hexadiene, 2-methyl-3-ethyl-1,3-butadiene, 3-methyl-1,3-pentadiene, 2-methyl-3-ethyl-1,3-pentadiene, 2-ethyl-1,3-pentadiene, 3-methyl-1,3-heptadiene, 3-octadiene, 3-butyl-1,3-octadiene, 3,4-dimethyl-1,3-hexadiene, 3-n-propyl-1,3-pentadiene, 4,5-diethyl-1,3-octadiene, 2-phenyl-1,3-butadiene, 2,3-diethyl-1,3-butadiene, 2,3-di-n-propyl-1,3-butadiene, 2-methyl-3-isopropyl-1,3-butadiene, chloroprene, fluoroprene, 2-methoxy-1,3-butadiene, 2-ethoxy-3-ethyl-1,3-butadiene, 2-ethoxy-3-methyl-1,3-hexadiene, decadiene, divinylbenzene, cyclohexene, vinylcyclohexene, benzocyclo-butene, norbornene, norbornadiene, dicyclopentadiene, ethylidene norbornene, and mixtures thereof;

C. Anionic Polymerization ethylene, styrene, α-methylstyrene, and p-vinyltoluene, conjugated dienes such as 1,3-butadiene, isoprene, 2,3-dimethyl-1,3-butadiene, 1,3-pentadiene, 1,5-hexadiene, 2,4-hexadiene, 1,3-hexadiene, 2-methyl-3-ethyl-1,3-butadiene, 3-methyl-1,3-pentadiene, 2-methyl-3-ethyl-1,3-pentadiene, 2-ethyl-1,3-pentadiene, 3-methyl-1,3-heptadiene, 3-octadiene, 3-butyl-1,3-octadiene, 3,4-dimethyl-1,3-hexadiene, 3-n-propyl-1,3-pentadiene, 4,5-diethyl-1,3-octadiene, 2-phenyl-1,3-butadiene, 2,3-diethyl-1,3-butadiene, 2,3-di-n-propyl-1,3-butadiene, 2-methyl-3-isopropyl-1,3-butadiene, divinylbenzene and divinyltoluene, methylmethacrylate, cyanoacrylate, and butylacrylate, acrylonitrile;

D. Ring Opening Polymerization ethylene oxide, propylene oxide, tetrahydrofuran, and trioxane, lactams, such as caprolactam, cyclic thioethers, epichlorohydrin and derivatives thereof, oxepans and oxetanes, lactones, lactides, cyclic anhydrides, and cyclic amines;

E. Metathesis Polymerization acyclic dienes, such as 1,3-butadiene, isoprene, 2,3-dimethyl-1,3-butadiene, 1,3-pentadiene, 1,5-hexadiene, 2,4-hexadiene, 1,3-hexadiene, 2-methyl-3-ethyl-1,3-butadiene, 3-methyl-1,3-pentadiene, 2-methyl-3-ethyl-1,3-pentadiene, 2-ethyl-1,3-pentadiene, 3-methyl-1,3-heptadiene, 3-octadiene, 3-butyl-1,3-octadiene, 3,4-dimethyl-1,3-hexadiene, 3-n-propyl-1,3-pentadiene, 4,5-diethyl-1,3-octadiene, 2-phenyl-1,3-butadiene, 2,3-diethyl-1,3-butadiene, 2,3-di-n-propyl-1,3-butadiene, 2-methyl-3-isopropyl-1,3-butadiene, chloroprene, fluoroprene, 2-methoxy-1,3-butadiene, 2-ethoxy-3-ethyl-1,3-butadiene, and 2-ethoxy-3-methyl-1,3-hexadiene, cyclic olefins such as cyclopentene, cyclohexene, and cyclooctene, and cyclic dienes such as cyclopentadiene, dicyclopentadiene, ethylidene norbornene, norbornene, norbornadiene, and cyclooctadiene;

F. Condensation or Step Growth Polymerization polyesters, polyanhydrides, polyacetals, polyacrylamide, polyamides, polyurethanes, polyureas, silk fibroin, cellulose, phenol-formaldehyde resins, urea-formaldehyde resins, polysulfides, polysiloxanes, polycarbonates, polyethers, polyimides, polyimines, polysaccharides, proteins, fluoro polymers, chlorinated polyolefins, and polytetrahydrofurans. Polymerized ethylene propylene diene monomer (EPDM) is an example of a light-permeable terpolymer preparable by this method and useful in the invention. In some embodiments, the method produces light permeable polycarbonates, polyurethanes, or polyethers.

In a "process for preparing a turbidity calibration standard," a polymerization reaction mixture may be formed in a container other than a light-permeable container and then transferred to the light-permeable container. Typically, the transfer is done before polymerizing of a monomer or co-monomer is completed. When a one layer standard is prepared (i.e., when in a process of the invention steps (a) and (b) are repeated 0 times, that is, not repeated), the one layer has a solid domain or a liquid domain distributed therein. The process can be done on a small scale for individual containers or adapted for manufacturing multiple containers of standards.

The phrase "reference value of turbidity" refers to a benchmark turbidity value that serves as a standard measurement of turbidity for calibrating a turbidity measuring instrument or for transferring calibration from one such instrument to another same or different type of instrument. The reference value of turbidity is used in calculations to determine a magnitude of deviation of a test value of turbidity from the reference value.

The phrase "test value of turbidity" refers to a test turbidity value, which may or may not be numerically different than a reference value of turbidity or benchmark turbidity value. The test value is used in calculations to determine a magnitude of deviation of the test value from the reference value of turbidity when calibrating a turbidity measuring instrument or transferring calibration from one such instrument to another same or different type of instrument. In some embodiments, the test value of turbidity is measured "at a time after" a time when the reference value of turbidity was measured. In these embodiments, the test value may be measured any time after the reference value is measured.

The term "transferring turbidity calibration" refers to a calibration process wherein a turbidity reference value obtained with a first turbidity measuring instrument is used to calibrate a second turbidity measuring instrument using a test value obtained with the second instrument.

The term "turbidity" includes hazes and more intense conditions (e.g., gradient of translucent conditions up to and including opaque conditions) where transmission of visible light through a medium such as a liquid is scattered, deflected, reflected, absorbed or any combination thereof. Generally, causes of turbidity include solid particles, groups of a liquid (i.e., a liquid domain), or gas bubbles suspended in the medium. For purposes of the invention, turbidity results from solid particles or liquid groups, but gas bubbles or vacuum pockets, if present, do not substantially contribute (i.e., contribute less than 5%) to a level turbidity. Turbidity measurements are based on transmitted light intensities, including scattered light intensities, compared to incident light intensities.

The term "haze" qualitatively means a finely divided powder (e.g., a dust) or light-weight liquid that slightly obscures transmission of visible light through an otherwise translucent medium such as a transparent liquid or air, and thereby imparts "cloudiness" to the medium when viewed in visible light with a naked eye. Haziness is a low level of turbidity.

Conditions of turbidity more intense than haziness produce a greater amount of light scattering, deflecting, or reflecting (with or without absorbing) than a haze such that a turbid medium having turbidity greater than a "haze" lacks transparent character to a naked eye. Turbidity, including haziness, is produced when a refractive index of a solid domain or liquid domain suspended in a layer is different than a refractive index of the layer. All other things being equal, the greater amount of the solid domain or liquid domain suspended in a layer, the greater the degree of turbidity in the layer. Similarly, all other things being equal, the higher a refractive index of the solid domain or liquid domain compared to a refractive index of the layer, the greater the degree of turbidity in the layer.

The term "turbidity measuring instrument" refers to any instrument used to measure turbidity, cloudiness, haziness, opaqueness, or the like of any liquid, including neat liquids such as water, suspensions of solids, liquids, or gas bubbles in a liquid, and the like. A turbidity measuring instrument includes a light source, at least one light detector, and a turbidity sample holder. A light-permeable container is dimensioned for being held by the sample holder. The light source, light detector, and sample holder may or may not be physically connected to each other. Examples of turbidity measuring instruments include nephelometers, turbidimeters, haze meters, and photographic systems comprising analog or digital cameras and a light source for obtaining analog or digital images of a turbidity sample. The photographic systems typically employ image processing software to characterize, standardize, or quantify the images. The turbidity measuring instruments include the system for image analysis of heterogeneous mixtures that is mentioned in Patent Cooperation Treaty International Patent Application Publication Number WO 2004/053468 A1.

A "first turbidity measuring instrument" and a "second turbidity measuring instrument" refer to different instruments, although a type, model, and manufacturer of the instruments may be identical. Generally, the first and second instruments should be the same type. In some embodiments, each instrument is a digital camera in independent communication with separate image processing software and a separate digital display. In other embodiments, each instrument is a nephelometer. In other embodiments, each instrument is a turbidimeter. In other embodiments, each instrument is a haze meter. In some embodiments, the first and second instruments will be from different manufacturers, but will function substantially in the same way and provide substantially the same result when measuring turbidity. For example, the first and second instruments could be nephelometers from different manufacturers, wherein the first and second instruments have the same type of light source, detector, detector angle, and so on. In other embodiments, the first and second instruments will be different models but from the same manufacturer. In other embodiments, the first and second instruments will be the same model and from the same manufacturer. The words of "first," "second," and the like do not imply any particular order or priority.

A turbidity calibration standard of the invention may be adapted within the metes and bounds of the invention for a particular turbidity assay method by choosing a particular solid domain or liquid domain, and choosing a particular light-transmission modulating amount thereof, choosing a particular number of layers, independently choosing a particular polymer or interpolymer comprising each layer, and choosing a particular container for containing them. It may be desirable to prepare and use several turbidity calibration standards ranged at different FNU for a particular assay method. A range of standards is useful for quantitatively calculating turbidity of a test sample.

One use of the turbidity calibration standards of the invention is to calibrate a turbidity measuring instrument. Two or more standards may be used to bracket or otherwise benchmark turbidity test measurement values of samples from chemical reactions, formulations, and quality testing samples.

Within the scope of the invention are turbidity calibration standards of the invention capable of emulating a wide variety of test samples that are in need of turbidity analysis. In one embodiment of the invention, a turbidity calibration standard is readily adapted to emulate a test sample of a product comprising a dispersion, suspension, emulsion, or the like. Examples of such products include:

a. inorganic colloidal suspensions used in chemical mechanical planarization (CMP) processing of silicon wafers during fabrication of semiconductor devices or solar energy panels, wherein the suspensions are comprised of silica, alumina, or cerium oxide;

b. aqueous polymer suspensions used in paints, coatings, adhesives, or sealants;

c. edible oil-in-water emulsions such as soybean oil, safflower oil, olive oil, medium-chain triglyceride oil, or fish oil based oil-in-water emulsions, which may contain flavor or color, used in beverages and food products such as sauces, dressings, and dietary supplements;

d. silicone-based emulsions used in hair cleaning (e.g., shampoos) and hair conditioning, hand lotions, surgical scrubs (i.e., cleaners), sealants, flexible potting compounds, and medical implants;

e. wax- or clay-containing aqueous emulsions used in preparing cosmetics;
f. soybean oil, safflower oil, olive oil, medium-chain triglyceride oil, or fish oil based oil-in-water emulsions used in intravenous drug delivery (e.g., anesthesia delivery) or parenteral delivery of nutrients to animal or human patients;
g. pigment-based suspensions used in conventional or inkjet printing;
h. silane-based oil-in-water emulsions used in water repellant applications;
i. inorganic colloidal suspensions used in pigmentation or sunscreens, wherein the suspensions may comprise, for example, titanium dioxide or zinc oxide;
j. homogenized whole milk dispersions or fat-reduced versions thereof;
k. water-in-oil emulsions or micro-emulsions used in lubricants or fuels;
l. oil-in-water emulsions used in ultrasound contrast imaging;
m. asphalt-based oil-in-water emulsions used in road maintenance;
n. oil-in-water emulsions used in herbicidal or insecticidal sprays;
o. oil-in-water emulsions used in household liquid cleaning products; and
p. oil-in-water emulsions wherein the oil is crude oil, motor oil—including synthetic and natural motor oil, gasoline, kerosene, diesel fuel, lubricating oil, and the like.

When testing turbidity of test samples of such products, ideally at least two, perhaps three or more, turbidity calibration standards of the invention at different concentrations of solid domain or liquid domain are prepared. Ideally, concentrations are chosen that are estimated to be below and above, and, perhaps, approximately at a concentration of the solid domain or liquid domain that is distributed, suspended, dispersed, or emulsed in the test samples.

When analyzing turbidity of a single-layer test sample, a single-layer turbidity calibration standard of the invention should ideally be used to calibrate a nephelometer or similar instrument. Likewise, when analyzing turbidity of a multi-layer test sample, a multi-layer turbidity calibration standard of the invention should ideally be used to calibrate the nephelometer or similar instrument.

In some embodiments, a method of analyzing turbidity of a turbidity calibration standard of the invention comprises moving a vertically positioned container such as a sample vial up and down while input light from a stationary source strikes a side wall of the container. Analysis of a two-layer turbidity standard using a nephelometer is illustrated in FIG. 1 (which is not the light scattering configuration that is used in the digital image calibration described in Example 16 and illustrated in FIG. 2). In FIG. 1, a turbidity calibration standard 10 is comprised of a container 11, a cap 12, a bottom layer 17, a top layer 15, and a meniscus 16. A nephelometer light source 35 of input light 34 is held stationary and the container 11 is moved along a vertical axis 32 so that the bottom layer 17, meniscus 16, and top layer 15 pass through the input light 34. A nephelometer detector 37 angled at 90° from the input light 34 detects scattered light 36. Transmitted light 38 exits container 11. A level of light transmitted or scattered relative to a level of input light will depend upon whether layer 15 or layer 17 is receiving the input light and there will be a transition phase when the input light reaches the meniscus 16.

In some embodiments, at room temperature (e.g., 25° C.), there is no substantial rag layer between any two layers of a multi-layer standard, there are no substantial vacuum or gas pockets in or between layers, and the single layer or each layer of the multi-layers is substantially non-flowable. A substantial rag layer is an intermediary zone of mixing of two layers at room temperature wherein turbidity of the zone differs from a turbidity of an unmixed portion of each of the two layers by more than 10 FNU as determined using ISO 7027. A substantial vacuum or gas pocket is a pocket in a layer at room temperature wherein the turbidity of the pocket differs from a turbidity of a pocket-free portion of the layer by more than 10 FNU as determined using ISO 7027. Between two layers, a substantial vacuum or gas pocket is a pocket between two layers at room temperature that causes a physical separation of the two layers at a wall of a light-permeable container, wherein the height of the pocket (i.e., the distance a top face of a bottom layer and a bottom face of a top layer of the two layers) is 2.0 mm or greater. A layer that is substantially non-flowable at room temperature is a layer at room temperature that does not move inside a light-permeable container more than 1.0 mm within 10 seconds of when the light-permeable container is turned upside down.

A solid domain or liquid domain may be selected for a particular application based on a sample of a chemical or formulation process being measured for turbidity and turbidity data that is being measured. In general, pigments useful in the invention are widely available from commercial sources such as Lansco Colors (formerly known as Landers Segal Color Company), Montevale, N.J., USA; Askash Chemicals & Dye-Stuffs, Inc., Glendale Heights, Ill., USA; and Sun Nano, Fremont, Calif., USA. In general, liquids useful in the invention are widely available from commercial sources such as Archer-Daniels Midland Company, Decatur, Ill., or APS Analytical Standards, Inc.

Average particle size, liquid domain group size, or a range therefor can be determined using a particle size analyzer instrument or a standard protocol method. Ideally, an ISO 13320 protocol is followed. Particle size analyzers are available commercially from suppliers such as ATA Scientific Pty Ltd, Lucas Heights, NSW, Australia or Beckman Coulter, Inc., Fullerton, Calif., USA.

Bench top and handheld refractometers are commercially available; suppliers include Mettler Toledo International Inc., Columbus, Ohio, USA.

Turbidity can be measured using commercially available digital cameras in communication with image processing software, nephelometers, turbidimeters, or haze meters. An example of a digital camera in communication with image processing software is a Nikon Coolpix 5700 digital camera in wired communication with Image J (shareware) image processing software residing on a computer in communication with a digital display; images can be printed or stored electronically. Nephelometers adapted for measuring turbidity of test samples arrayed in a 96-well format, an example of a parallel turbidity assay method format, include NEPHEL Ostar Microplate Reader available from BMG LABTECH GmbH, Offenburg, Germany. The NEPHEL Ostar Microplate Reader uses a wavelength of 635 nm and can accept up to 384 multi-well parallel turbidity measurement plates. Other nephelometers are commercially available from suppliers such as Cole-Parmer Instrument Company, Vernon Hills, Ill., USA. Temperature-dependent turbidity measurements may include a light source, temperature-controlled test cell, and a light sensor. Another useful turbidity measuring instrument is a system for image analysis of heterogeneous mixtures using combinatorial techniques is mentioned in Patent Cooperation Treaty International Patent Application Publication Number WO 2004/053468 A1.

For purposes of determining the metes and bounds of the invention, should a need arise, an ISO 7027 method should be used as the method for measuring turbidity. The standard ISO 7027 method that specifies a light emitting diode (LED) light source with a near infrared wavelength of 860 nanometers (nm) with a spectral bandwidth of less than or equal to 60 nm and recording turbidity in FNU based on light scattered at a 90° angle between a detector and an incident light axis (International Standards Organization, Water Quality—Determination of Turbidity, ISO 7027, Geneva, Switzerland, 1999).

A SYLGARD® (Dow Corning Corporation, Midland, Mich., USA) 184 Silicone Elastomer Kit may be purchased from a supplier such as Ellsworth Adhesives, Sterling Heights, Mich., USA (e.g., item number 2065622). (Herein, generically referred to as a "silicone-based polymer." SYLGARD® 184 is one of a number of different light-permeable silicone-based polymers.) The kit is comprised of a clear colorless liquid silicone base (184 resin base) and a clear colorless liquid curing agent (184 curing agent). The 184 resin base is comprised of >60% by weight of dimethyl siloxane, dimethylvinyl-terminated (Chemical Abstracts Registry Number (CAS RegNo.) [68083-19-2]); 30.0-60.0% by weight of dimethylvinylated and trimethylated silica (CAS RegNo. [68988-89-6]); 1.0-5.0% by weight of tetra(trimethylsiloxy) silane (CAS RegNo. [3555-47-3]; <1.0% by weight of ethylbenzene; and 0.7% by weight of xylene. The 184 curing agent is comprised of 40.0-70.0% by weight of dimethyl, methylhydrogen siloxane (CAS RegNo. [68037-59-2]); 15.0-40.0% by weight of dimethyl siloxane, dimethylvinyl-terminated; 10.0-30.0% by weight of dimethylvinylated and trimethylated silica; 1.0-5.0% by weight of tetramethyl tetravinyl cyclotetrasiloxane (CAS RegNo. [2554-06-5]); 0.3% by weight of xylene; and <0.1% by weight of ethylbenzene. The 184 resin base and 184 curing agent are mixed, ideally in a 10:1 ratio, and allowed to cure at room temperature over 48 hours or heat cured for 10 minutes at 150° C.; 20 minutes at 125° C.; or 45 minutes at 100° C.

Preparations and examples are described below.

Preparation 1

A Silicone-Based Polymer

In a 100-mL glass beaker is mixed 45 g of 184 resin base and 5 g of 184 curing agent. A resulting mixture is sonicated (i.e., subjected to ultrasound) in an ultrasonic cleaning bath (Model 450, E/MC Corporation) to break up any bubbles at a surface of the mixture. The mixture is then placed in a vacuum desicator fitted with a hose that is connected to a plastic quick connect. The quick connect is to allow a quick release of air back into the desicator, e.g., over 5 to 10 seconds. The desicator is evacuated under house vacuum (15 mm to 20 mm Hg) over several minutes to allow bubbles to grow, rise, and release and then repressurized with air about five times until no additional bubbles are observed. A portion of the degassed mixture is then poured into a 100-mL plastic syringe barrel fitted with a narrow bore needle, but attempts to plunge the mixture through the needle fail. Accordingly, the mixture is poured from the syringe barrel into a vial (about 4.3 cm in height) and the vial is capped. If necessary, the vial is placed into a 10-mL beaker and sonicated to break any new bubbles that form. The degassed mixture is set aside and allowed to cure at room temperature over 48 hours to give a silicone-based polymer. The polymer is characterized by a meniscus.

Preparation 2

A Silicone-Based Polymer

In a manner analogous to the procedure of Preparation 1, 100.12 g of 184 resin base and 10.00 g of 184 curing agent is mixed in 150-mL glass beaker. The resulting mixture is degassed for 15 minutes under house vacuum, and an aliquot is then poured into a 100-mL syringe with a capped tip to prevent escape of the mixture. The syringe is then inverted and a syringe plunger inserted. The mixture is allowed to collect on a rubber sealed end of the plunger. The plunger is advanced slowly to expel excess air without trapping bubbles. The syringe is placed under house vacuum to remove any bubbles that may form to give a degassed mixture. A 16-gauge tapered plastic tip (I&J Fisnar part number 560010K) is attached to the barrel, and the degassed mixture is then pushed into the bottom of an about 4.3 cm height vial until the vial is filled to between about 2.8 cm and about 3.0 cm. If necessary, the vial is placed into a 10-mL beaker and sonicated to break any new bubbles that form. The degassed mixture is set aside and allowed to cure at room temperature over 48 hours to give a silicone-based polymer. The polymer is characterized by a meniscus.

Preparation 3

Talc (catalog number T4-500, Fisher Scientific) is ground by hand for 2 minutes to stabilize the talc's particle size distribution, yielding ground talc.

Example 1

Single layer turbidity standard comprising 10.0% weight/weight of talc Distributed in a silicone-based polymer and contained in a transparent glass vial To a 30-mL beaker is added gravimetrically a 9.00 g portion of the degassed mixture of Preparation 1. To the top of the degassed mixture is added 1.00 g of the ground talc of Preparation 3 to give a new mixture. The new mixture was hand mixed with a spatula, and then placed in an ultrasonic bath and sonicated. The resulting suspension is then placed in a vacuum desicator fitted with a hose that is connected to a plastic quick connect. The quick connect is to allow a quick release of air back into the desicator, e.g., over 5 to 10 seconds. The desicator is evacuated under house vacuum (15 mm to 20 mm Hg) over several minutes to allow bubbles to grow, rise, and release and then repressurized with air about five times until no additional bubbles are observed to give a degassed suspension. A portion of the degassed suspension is then poured into a vial (about 4.3 cm in height) and the vial is capped. If necessary, the vial is placed into a 10-mL beaker and sonicated to break any bubbles that form. The degassed suspension is set aside and allowed to cure at room temperature over 48 hours to give a silicone-based polymer comprised of talc distributed in a silicone-based polymer. The resulting standard is characterized by a meniscus and contains 10.0% by weight of talc.

Example 2

Single layer turbidity standard comprising 1.0% weight/weight of talc distributed in a silicone-based polymer and contained in a transparent glass vial is prepared in a manner analogous to Example 1 except 9.90 g of the degassed mixture of Preparation 1 and 0.10 g of talc are used and the mixing step with spatula and ultrasonic bath is easier.

Example 3

Single layer turbidity standard comprising 0.104% weight/weight of talc distributed in a silicone-based polymer and contained in a transparent glass vial is prepared in a manner analogous to Example 1 except 10.0006 g of the degassed mixture of Preparation 1 and 0.01004 g of talc are used and the mixing step with spatula and ultrasonic bath is easier.

Example 4

Single layer turbidity standard comprising 10.081% weight/weight of talc distributed in a silicone-based polymer and contained in a transparent glass vial To a 30-mL beaker is added gravimetrically a 9.0047 g portion of the degassed mixture of Preparation 2. To the top of the degassed mixture is added 1.0095 g of the ground talc of Preparation 3 to give a new mixture. The new mixture was hand mixed with a spatula, and then placed in an ultrasonic bath and sonicated. The resulting suspension is placed under house vacuum for 15 minutes to remove further gas bubbles. An aliquot is then poured into a 100-mL syringe with a capped tip to prevent escape of the mixture. The syringe is then inverted and a syringe plunger inserted. The suspension is allowed to collect on a rubber sealed end of the plunger. The plunger is advanced slowly to expel excess air without trapping bubbles. The syringe is placed under house vacuum to remove any bubbles that may form to give a degassed suspension. A 16-gauge tapered plastic tip (I&J Fisnar part number 56001OK) is attached to the barrel, and the degassed suspension is then pushed into the bottom of an about 4.3 cm height vial until the vial is filled to between about 2.8 cm and about 3.0 cm. If necessary, the vial is placed into a 10-mL beaker and sonicated to break any new bubbles that form. The degassed suspension is set aside and allowed to cure at room temperature over 48 hours to give talc distributed in a silicone-based polymer. The standard is characterized by a meniscus and contains 10.081% by weight of talc.

Example 5

Single layer turbidity standard comprising 1.001% weight/weight of talc distributed in a silicone-based polymer and contained in a transparent glass vial is prepared in a manner analogous to Example 4 except 9.9089 g of the degassed mixture of Preparation 2 and 0.1002 g of talc are used and the mixing step with spatula and ultrasonic bath is easier.

Example 6

Single layer turbidity standard comprising 0.101% weight/weight of talc distributed in a silicone-based polymer and contained in a transparent glass vial is prepared in a manner analogous to Example 4 except 10.0035 g of the degassed mixture of Preparation 2 and 0.0101 g of talc are used and the mixing step with spatula and ultrasonic bath is easier.

Example 7

In a manner analogous to the procedures of Examples 4 to 6, single layer turbidity standards comprised of 10%, 1%, and 0.1% by weight of silica powder (Fiber Optic Center, Inc., Angstrom Sphere Mono-dispersed Silica Powder with 1.0 micrometer particle size; item number S102P100-01), which replaced the talc used in Examples 4 to 6 are prepared. Hand mixing fails to prevent clumping of silica and settling of clumped silica at the bottom of each beaker. The mixtures are mixed on a dual-axis mixer (FlackTek Inc. SpeedMixer DAC 150 FVZ-K) at 1000 revolutions per minute (RPM) for 1 minute, 2400 RPM for 1 minute, and then 3000 RPM for 5 minutes. After this mixing, some silica is still observed clumped at the bottom of the beakers.

Example 8

Sequentially interfaced two layer turbidity standard comprising a top layer comprised of 10.081% weight/weight of talc distributed in a silicone-based polymer and a bottom layer comprised of a silicone-based polymer, wherein the top layer is characterized, in part, by a bottom face and the bottom layer is characterized, in part, by a top face, which is interfaced to the bottom face of the top layer, and contained in a transparent glass vial To a top face of the silicone-based polymer of Preparation 2 is added a portion of the degassed liquid suspension prepared in Example 4. If necessary, the vial is placed into a 10-mL beaker and sonicated to break any new bubbles that form. The degassed liquid suspension is set aside and allowed to cure at room temperature over 48 hours. The resulting sequentially interfaced two-layer standard is comprised of a bottom layer interfaced with a top layer. The bottom layer is comprised of a silicone-based polymer. The top layer is comprised of 10.081% by weight of talc distributed in a silicone-based polymer. The standard is characterized by a meniscus at the interface between the top and bottom layers and the top layer contains 10.081% by weight of talc. The bottom layer does not contain talc.

Example 9

Sequentially interfaced two layer turbidity standard comprising a top layer comprised of a silicone-based polymer and a bottom layer comprised of 1.001% weight/weight of talc distributed in a silicone-based polymer, wherein the top layer is characterized, in part, by a bottom face and the bottom layer is characterized, in part, by a top face, which is interfaced to the bottom face of the top layer, and contained in a transparent glass vial To a top face of the 1.001% weight/weight of talc in a silicone-based polymer of Example 5 is added the degassed mixture of Preparation 2. If necessary, the vial is placed into a 10-mL beaker and sonicated to break any new bubbles that form. The degassed mixture is set aside and allowed to cure at room temperature over 48 hours. The resulting sequentially interfaced two-layer standard is comprised of a bottom layer interfaced with a top layer. The bottom layer is comprised of 1.001% by weight of talc distributed in a silicone-based polymer. The top layer is comprised of a silicone-based polymer. The standard is characterized by a meniscus at the interface between the top and bottom layers and the bottom layer contains 1.001% by weight of talc. The top layer does not contain talc.

Example 10

Sequentially interfaced three layer turbidity standard comprising a top layer comprised of 10.081% weight/weight of talc distributed in a silicone-based polymer; a middle layer comprised of a silicone-based polymer; and a bottom layer comprised of 1.001% weight/weight of talc distributed in a silicone-based polymer, wherein the top layer is characterized, in part, by a bottom face; the middle layer is characterized, in part, by a top face, which is interfaced to the bottom face of the top layer, and a bottom face; and the bottom layer is characterized, in part, by a top face, which is interfaced to the bottom face of the middle layer, and contained in a transparent glass vial In a procedure analogous to the method of Example 9, a two-layer standard comprised of a bottom layer interfaced with a top layer is prepared in a vial having a height of 9.0 cm. The bottom layer is comprised of 1.001% by weight of talc distributed in a silicone-based polymer. The top layer of the two layer standard is comprised of a silicone-based polymer. To a top face of the top layer of the two-layer standard is added a portion of the degassed liquid suspension prepared in Example 4. If necessary, the vial is placed into a beaker and sonicated to break any new bubbles that form. The degassed liquid suspension is set aside and allowed to cure at room temperature over 48 hours. The resulting sequentially interfaced three-layer standard is comprised of a bottom layer interfaced with a middle layer, which in turn is interfaced with a top layer. The bottom layer of the three layer standard is comprised of 1.001% by weight of talc distributed in the silicone-based polymer. The middle layer of the three layer standard is comprised of the silicone-based polymer. The top layer of the three layer standard is comprised of 10.081% by weight of talc distributed in a silicone-based polymer. The standard is characterized by a first meniscus at the interface between the top and middle layers and a second meniscus between at the interface between the middle and bottom layers. The top layer contains 10.081% by weight of talc. The middle layer does not contain talc. The bottom layer contains 1.001% by weight of talc.

Example 11

Sequentially interfaced four layer turbidity standard comprising a top-most layer comprised of a silicone-based polymer; an upper middle layer interfaced with the top-most layer and a lower middle layer, the upper middle layer comprised of 10.081% weight/weight of talc distributed in a silicone-based polymer; a lower middle layer interfaced with the upper middle layer and a bottom layer, the lower middle layer comprised of a silicone-based polymer; and a bottom layer comprised of 1.001% weight/weight of talc distributed in a silicone-based polymer, wherein the top-most layer is characterized, in part, by a bottom face; the upper middle layer is characterized, in part, by a top face, which is interfaced to the bottom face of the top-most layer, and a bottom face; the lower middle layer is characterized, in part, by a top face, which is interfaced with the bottom face of the upper middle layer, and a bottom face; and the bottom layer is characterized, in part, by a top face, which is interfaced to the bottom face of the lower middle layer, and contained in a transparent glass vial To the top of the top layer of Example 10 in the 9 cm vial is added an aliquot of the degassed mixture of Preparation 2. If necessary, the vial is placed into a 10-mL beaker and sonicated to break any new bubbles that form. The degassed mixture is set aside and allowed to cure at room temperature over 48 hours. The resulting sequentially interfaced four-layer standard is comprised of a top-most layer comprised of a silicone-based polymer; an upper middle layer interfaced with the top-most layer and a lower middle layer, the upper middle layer comprised of 10.081% weight/weight of talc distributed in a silicone-based polymer; a lower middle layer interfaced with the upper middle layer and a bottom layer, the lower middle layer comprised of a silicone-based polymer; and a bottom layer comprised of 1.001% weight/weight of talc distributed in a silicone-based polymer.

Example 11A: continuing in the way of Examples 8 and 11, a sequentially interfaced five layer turbidity standard is prepared that is similar to the four layer standard of Example 11 except the five layer standard of Example 11A is further comprised of a fifth, "super-top" layer comprised of 10.081% weight/weight of talc distributed in a silicone-based polymer, wherein the super-top layer is interfaced with a top-most layer of Example 11.

Example 12

Single layer turbidity standard comprising 0.101% weight/weight of styrene-divinylbenzene sub-micrometer copolymer beads distributed in a silicone-based polymer and contained in a transparent glass vial In a manner analogous to Example 6 except 0.0101 g of styrene-divinylbenzene sub-micrometer copolymer beads are used in place of talc. The resulting standard is characterized by a meniscus and contains 0.101% by weight of styrene-divinylbenzene sub-micrometer copolymer beads.

Example 13

Single layer turbidity standard comprising 0.101% weight/weight of a powdered iron(II) oxide distributed in a silicone-based polymer and contained in a transparent glass vial In a manner analogous to Example 6 except 0.0101 g of a powdered iron(ii)oxide are used in place of talc. The resulting standard is characterized by a meniscus and contains 0.101% by weight of a powdered iron(ii)oxide.

Example 14

Single layer turbidity standard comprising 0.101% weight/weight of carbon nanotubes distributed in a polymethylmethacrylate (PMMA) polymer and contained in a transparent glass vial In a manner analogous to Example 6 except 0.0101 g of carbon nanotubes are used in place of talc and a degassed methyl methacrylate is used in place of the degassed mixture of Preparation 2. The methyl methacrylate is polymerized using a conventional procedure such as a method of U.S. Pat. No. 5,324,802; 3,113,114; or 2,471,959 to give a single layer turbidity standard comprising 0.101% weight/weight of carbon nanotubes distributed in a PMMA polymer.

Example 15

Single layer turbidity standard comprising 0.101% weight/weight of water distributed in a silicone-based polymer and contained in a transparent glass vial In a manner analogous to Example 4 except 10.0035 g of the degassed mixture of Preparation 2 and 0.0101 g of water are used in place of talc and the curing of the silicone-based polymer is carried out while a suspension of water in the silicone-based polymer is mixed on a dual-axis mixer (Flack-Tek Inc. SpeedMixer DAC 150 FVZ-K) at 1000 RPM. The resulting standard is characterized by a meniscus and contains 0.101% by weight of water distributed therein.

When carrying out a procedure of the Examples 1 to 15, a monomer(s) and a solid domain may be weighed and mixed in a weighing pan. It is helpful to use a metal weighing pan (e.g., aluminum weighing pan, Fisher Scientific, Product Number 08-732) rather than a plastic pan to minimize inhibition of polymerizations by compounds that may be leached from the plastic pan. When using a spatula to mix materials in the weighing pan or in a beaker, use a clean spatula and fold a mixture carefully to avoid introducing an undue number of bubbles. Use the same spatula in each mixing step to maintain relative concentrations of ingredients in a mixture. When degassing a mixture, the weighing pan may be placed in a vacuum desicator, preferably on a paper towel. The desicator may be evacuated with house vacuum for a minute while observing small bubbles forming and rising to a top surface of the mixture. Release the vacuum quickly to allow the bubbles to break, which may take 15 seconds. Repeat evacuation/release iterations until no more bubbles are observed.

Example 16

Initial turbidity instrument base calibration procedure and subsequent field calibration of the same instrument in the same or at a different location This example relates to a two-step calibration procedure comprising (A) an initial base calibration operation of a turbidity measuring instrument using three sets of turbidity samples, each set comprising three independent turbidity calibration standards and a "blank" polymer, and producing data that comprises a base calibration model; and (B) a subsequent field calibration operation with the same turbidity measuring instrument using one of the sets of turbidity samples and producing field calibration data. An optional third operation is described below in Example 17, wherein a calibration equation is determined for the instrument using the base calibration data and the field calibration data.

Three turbidity sample sets are described in this example and they will be generally referred to here as "Sample Sets." Each sample set is comprised of turbidity samples, which will be generally referred to here as "Samples." Sample Set 1 is comprised of Samples A1, B1, C1, and D1. Sample Set 2 is comprised of Samples A2, B2, C2, and D2. Sample Set 3 is comprised of Samples A3, B3, C3, and D3. Sample A1 is comprised of the "blank" polymer of Preparation 2 in a vial; Sample B1 is comprised of the 0.101% single layer turbidity standard of Example 6; Sample C1 is comprised of the 1.001% single layer turbidity standard of Example 5; and Sample D1 is comprised of the 10.081% single layer turbidity standard of Example 4. (See below for Examples 4 to 6.) Samples A2, B2, C2, and D2 and Samples A3, B3, C3, and D3 are independently comprised of a blank polymer, a 0.1%-level turbidity standard, a 1.0%-level turbidity standard, and a 10.0%-level turbidity standard that are separately prepared according to the methods of Preparation 2 and Examples 4 to 6, respectively. Due to slight differences in technique, amounts, times, and the like, there will be slight variations between Samples A1, A2, and A3; between Samples B1, B2, and B3; between Samples C1, C2, and C3; and between Samples D1, D2, and D3. Variations between Samples A1, A2, and A3 will likely be less pronounced than variations within the other groups of Samples because Samples A1, A2, and A3 do not contain any solid domain or liquid domain.

(A) Initial Base Turbidity Measuring Instrument Calibration Operation

The initial base calibration operation accounts for small variations between Samples A1, A2, and A3; between Samples B1, B2, and B3; between Samples C1, C2, and C3; and between Samples D1, D2, and D3. Steps comprising the initial base calibration operation are described here:

1. In an initial base calibration, all samples are run on the same instrument on the same day with no changes in any settings. (An assumption is that the instrument is substantially the same during the data collection with all samples.) The exposure time is noted, as all calibration runs use the same exposure time. The instrument that is used is any nephelometer or an instrument equipped with a camera-based digital imaging unit such as using a Nikon Coolpix 5700 digital camera in communication with Image J image processing software to process the image data and a display for displaying the unprocessed or processed images. In this example, the instrument is an instrument equipped with a camera-based digital imaging unit such as using a photography light source and a Nikon Coolpix 5700 digital camera in communication with Image J image processing software to process the image data and a display for displaying the unprocessed or processed images. The photography light source is a 22.9 cm fluorescent bulb positioned so that perpendicular to a vertical plane running from the sample to the camera lens and about 15 cm in front of, and about 10 cm above, a base of a vial that contains a sample. The camera is set in an aperture preferred mode with an f-stop of greater than 4.5 to provide sufficient depth of field. The shutter speed is varied with the conditions, but is generally between $\frac{1}{60}$ and $\frac{1}{250}$ of a second. The camera is set on a lab jack to reduce shaking and the lens is in a telephoto position. Each image from the camera is saved as a tag image bitmap file (TIFF) to a computer data memory drive. Temperature is about 20° C. All samples are run 5 times each. An average turbidity for each sample in is calculated. A median of the 5 runs with a sample is determined and selected as a base measurement of turbidity for that sample. Grayscale data collected for each sample are shown below in Table 1.

TABLE 1

Example data collected during the initial calibration.

| Sample | Median Grayscale from 5 replicates |
|---|---|
| A1 | 2 |
| B1 | 80 |
| C1 | 150 |
| D1 | 253 |
| A2 | 6 |
| B2 | 78 |
| C2 | 148 |
| D2 | 254 |
| A3 | 5 |
| B3 | 83 |
| C3 | 153 |
| D3 | 250 |

2. Once the grayscale data are obtained, a calibration scale is prepared. For example, a range comprising a lower limit value of 0 to an upper limit value of 100 is selected, wherein the range value 0 is black in a grayscale and the range value 100 is white in a grayscale.

3. Next, it is defined what median grayscale value will represent 0 and what median grayscale value will represent 100. This can be done a number of ways. For example, the blackest sample from Table 1 is selected to be 0 and the whitest sample is selected to be 100. For the example data above, A1 grayscale value=2, the blackest sample, and D2 grayscale value=254, the whitest sample. The two ends of a range are chosen such that most of expected future data will fall in the range, which is defined as being from a low end value of the range to a high end value of the range and including the end values. It is not, however, required by mathematics used to calibrate an instrument that every datum for a sample falls in a selected range.

Figure 2:
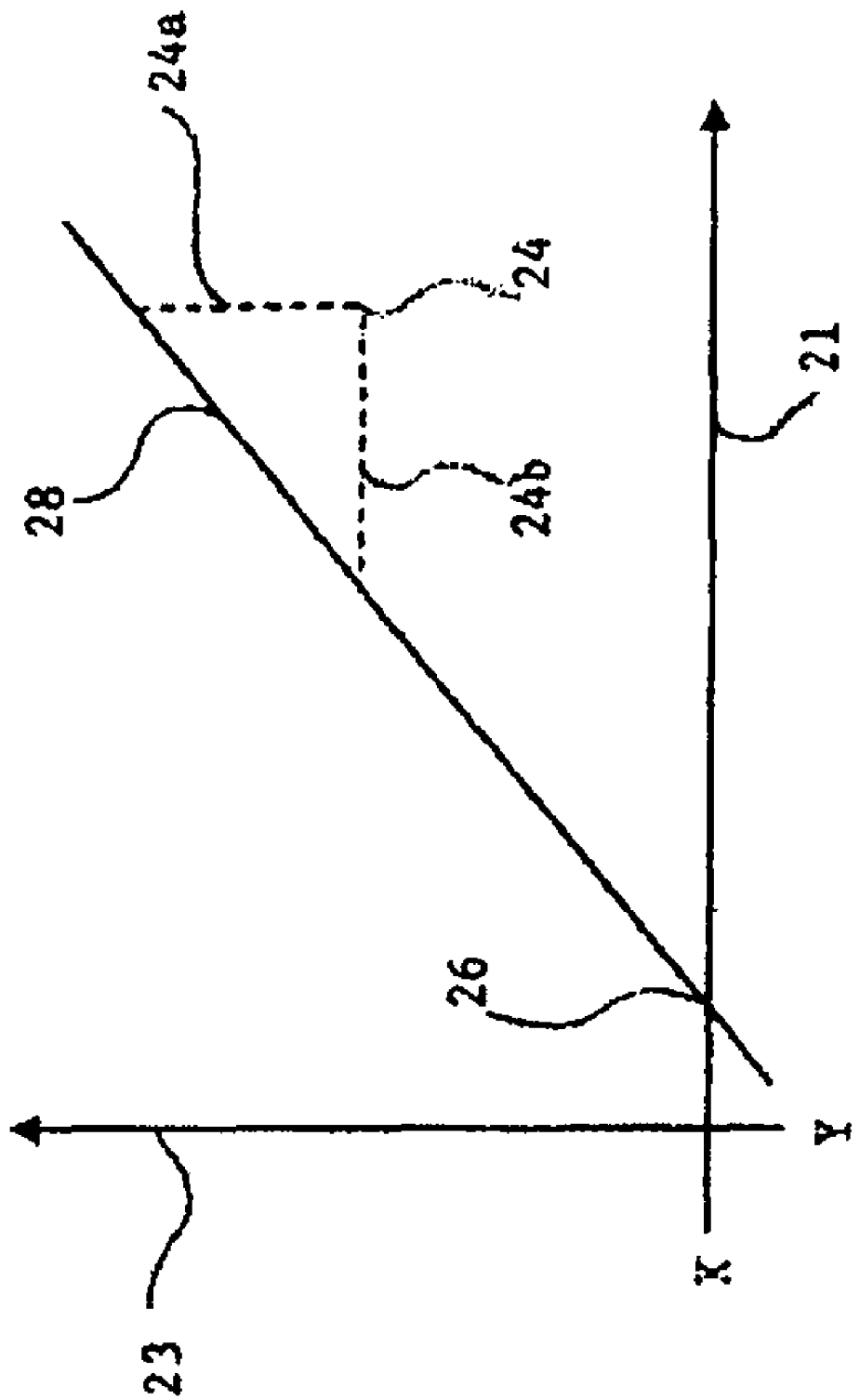
FIG. 2 illustrates a relationship between raw grayscale turbidity measurements and grayscale turbidity measurements after calibration to a nominal scale from 0 to 100.

4. Now, all of the data collected during the initial base calibration operation are calibrated to the range comprising the calibration scale via a slope and intercept as graphically shown in FIG. 2. In FIG. 2, a slope 24 of a line 28 is calculated by dividing length 24a by length 24b. Line 28 is generated from data plotted on an x-axis 21 and a y-axis 23 has an intercept 26 on the x-axis 21. To generate the line 28, raw turbidity measurement data of x-axis 21 are plotted against calibration scale turbidity values of y-axis 23.

The necessary data are:
   lowR=measured low-raw (Sample A1 in Table 1, grayscale=2)
   highR=measured high-raw (Standard D2 in Table 1, grayscale=254)
   lowC=set low calibration equal to 0 (i.e., correlates the lowR value to the lowC value to set the lower limit of the range of the calibration scale)
   highC=set high calibration equal to 100 (i.e., correlates highR value to the highC value to set the upper limit of the range of the calibration scale)

The calibration model is:

calibrated standard clarity=(slope*Raw clarity)+intercept where
   "*" means times (i.e., as in multiplication)
   "+" means plus (i.e., as in addition)
   slope=(highC−lowC)/(highR−lowR)
   intercept=lowC−(slope*lowR)

For the example data above
   slope=(100−0)/(254−2)=0.3968
   intercept=0−(0.3968*2)=−0.7936

These calibrated results may be saved for use in mathematical equations used to calibrate raw data to a calibration scale. Applying this formula to the example standards from Table 1 gives the results in Table 2.

TABLE 2

Calibration applied to the Initial Calibration Data.

| Standard | Median Grayscale from 5 replicates | Grayscale, initial calibration |
|---|---|---|
| A1 | 2 | 0 |
| B1 | 80 | 30.95 |
| C1 | 150 | 58.73 |
| D1 | 253 | 99.60 |
| A2 | 6 | 1.59 |
| B2 | 78 | 30.16 |
| C2 | 148 | 57.93 |
| D2 | 254 | 100 |
| A3 | 5 | 1.19 |
| B3 | 83 | 32.14 |
| C3 | 153 | 59.92 |
| D3 | 250 | 98.41 |

5. As mentioned above, turbidity of Sample Sets 1 to 3 has been measured. Sample Sets 1 and 2 are used as turbidity calibration standards of the invention in below Examples 17 and 18, which use the instrument as that mentioned here in Example 16. Alternatively, Sample Sets 2 and 3 are used as turbidity calibration standards of the invention as described below in Example 19 for transferring calibration from the instrument mentioned here in Example 16 to a different instrument of the same model and manufacturer.

(B) Field Turbidity Measuring Instrument Calibration Operation

After the initial base calibration operation, a field calibration is run monthly or more or less often depending upon the particular circumstances. The instrument described above for operation (A) has been moved from manufacturing location to a field location. Sample Sets 1 and 2 have also been moved to the field location as components of a kit that further contains information about the turbidity measurements of the standards of Sample Sets 1 and 2 measured with the turbidity measuring instrument as described above and instructions for use of the standards in calibrating the turbidity measuring instrument in the field. Once calibrated in the field, the turbidity measuring instrument will be ready for reliably measuring turbidity of test samples.

1. A field instrument runs two sets (Sample Sets 1 and 2) of four field standards each. Each standard is run 5 times (placing each standard back and forth between its storage holder and the instrument holder each time). Exposure time is set to be the same as the exposure time used in operation (A) when the initial base calibration was conducted. Raw uncalibrated field measurement data are generated for each standard using the procedure of the initial base calibration operation.

2. An average turbidity for each replicate of each standard is determined. A degree of variation of turbidity values of the 5 replicate measurements is examined for each standard. If the degree of variation for any one standard is larger than a maximally acceptable amount, the calibration is failed.

3. Median turbidity values for standards A and D are determined and compared to the initial base calibration range of operation (A). If any standard fails to fall in the range, the calibration is failed.
   0 grayscale<median turbidity value of A<15 grayscale
   240 grayscale<median turbidity value of D<255 grayscale 4. Compare the median turbidity value of standard A and median turbidity value of D to their respective previous median turbidity value calibrations using conventional quality control software. If there is an unacceptable degree of deviation between the initial base calibration median value and the field calibration median value, the calibration is failed.

5. If the calibration is failed, store the median turbidity value of A and median turbidity value of D for use with the field instrument and apply these data when calibrating future images obtained with the field instrument.

If the calibration is failed, adjust at least one setting on the turbidity measuring instrument and rerun the field turbidity measuring instrument calibration procedure.

This example illustrates a calibration procedure that could be used by, for example, a turbidity measuring instrument manufacturer or inventor for calibrating a newly manufactured instrument (i.e., the base calibration instrument) and, then, shipping the instrument to a purchaser with a set of the field turbidity calibration standards, which would allow a purchaser of the instrument to recalibrate the instrument (now a field instrument) before beginning field operation of the instrument. In Example 16, the instrument used for initial base calibration is identical to the instrument used for field calibration (i.e., the instruments are one and the same).

Example 17

A field re-calibration procedure for periodically recalibrating the field turbidity measuring instrument mentioned in Example 16

After a field calibration has been performed as in Example 16, all pixels in future images may be calibrated. This may be accomplished as follows. Assume, for example, that the field standards A2 and D1 of Example 16 are used and the field calibration of operation (B) of Example 16 did not fail. The data from Example 16 for the standards are listed in Table 3.

TABLE 3

Example Data for Field Calibration

| Standard | Calibrated Value, Calib_low, Calib_high | Field Measurement, Field_low, Field_high |
|---|---|---|
| A2 | 1.59 | 5 |
| D1 | 99.60 | 250 |

Correct each pixel (i,j) using a slope and intercept using the following equation:

$$\text{calibrated}(i,j) = [\text{slope}_f * \text{grayscale}(i,j)] + \text{intercept}_f$$

where
  grayscale(i,j)=measured grayscale for pixel i,j in the new image
  $\text{slope}_f$=(Calib_high−Calib_low)/(Field_high−Field_low)= 0.400
  $\text{intercept}_f$=Calib_low−($\text{slope}_f$*Field_low)=−0.41
  calibrated(i,j)=calibrated pixel intensity
  the subscript f indicates 'field calibration'

For example, assume pixel 200,45 has a grayscale of 64. The calibrated value at that pixel is $$\text{calibrated value}(200,45) = (0.400*64) - 0.41 = 25.19$$

As mentioned in Example 16 in reference to mathematics of calibration, a calibrated value at a pixel can be outside the range of 0-100 and still be acceptable.

Optionally, color scale values instead of grayscale values are calibrated.

If the calibration is failed, adjust at least one setting on the turbidity measuring instrument and rerun the field turbidity measuring instrument calibration procedure.

In Example 17, the instrument used for field re-calibration is identical to the instrument used for initial base calibration and field calibration in Example 16 (i.e., the instruments of Examples 16 and 17 are one and the same).

Example 18

A quality control re-calibration procedure for calibrating the field turbidity measuring instrument mentioned in Examples 16 and 17 on a routine basis during periods of time when the instrument is used to measure turbidity of test samples.

A quality control re-calibration procedure may be run once per week, once per day, or the like, depending on particular circumstances, as follows:
1. Using the same field instrument and Sample Sets 1 and 2 as mentioned in Examples 16 and 17, collect images on the four field standards of Sample Sets 1 and 2. Runs are 5 times for each standard (placing the standard back and forth between its storage holder and the instrument holder each time). The exposure time is set to be the same as when the initial calibration was conducted (see Example 16).
2. Apply the calibration equation of Example 16 and determine the turbidity value for the largest phase (normal sample analysis). Compare the range of the turbidity values for the B standards. Compare the range of the turbidity values for the C standards. If either range is unacceptably large for the circumstances, fail the quality control. Next, compare the median turbidity of the B standards to the predetermined range (see Example 16).
3. Compare the median turbidity of the C standards to the predetermined range (see Example 16). For example:
    (75% of median turbidity of B standards)<median turbidity of B standards<(125% of median turbidity of B standards); and
    (75% of median turbidity of C standards)<median turbidity of C standards<125% of median turbidity of C standards).
4. Optionally, the turbidity results may be stored for evaluation in an external quality control analysis program.

If the calibration is failed, adjust at least one setting on the turbidity measuring instrument and rerun the field turbidity measuring instrument calibration procedure.

The instrument of Example 16 is the one and the same as the instrument of Example 17 and the one and the same as the instrument of Example 18.

Example 19

Transfer of an initial base calibration from a first turbidity measuring instrument to provide an initial base calibration of a second turbidity measuring instrument, which is in the field, wherein the first and second instruments are of the same model and manufacturer, but are not the same instruments.
1. A field turbidity measuring instrument that is different than the turbidity measuring instrument of Examples 16 to 18 runs the four field standards each of Sample Sets 2 and 3. Sample Sets 2 and 3 are provided to the field location as components of a kit that further contains information about the turbidity measurements of the standards of Sample Sets 2 and 3 measured with the turbidity measuring instrument as described above in Example 16 and instructions for use of the samples in calibrating the field turbidity measuring instrument. Once calibrated, the field turbidity measuring instrument will be ready for reliably measuring turbidity of test samples and producing turbidity data that can be compared, if desired, to turbidity data of different test samples produced with the turbidity measuring instrument of Examples 16 to 18. Each standard is run 5 times (placing the standard back and forth between its storage holder and the instrument holder each time). The Sample Sets 2 and 3 are the same as Sample Sets 2 and 3 that are mentioned in Example 16 (i.e., assume Sample Set 2 had not been moved to the field location mentioned in Example 16, but Sample Sets 2 and 3 of Example 16 were moved to a different field location). Exposure time is set to be the same as when the initial base calibration was conducted as described in operation (A) of Example 16. Generate raw uncalibrated field measurement data using the procedure of the initial base calibration operation for each standard.
2. Determine the average turbidity for each replicate measurement of each standard. Examine how much the turbidity varies over the 5 replicate measurements for each standard. If the range for any one standard is larger than a maximally acceptable amount, the calibration is failed.
3. Separately compare the median turbidity of standards A and the median turbidity of standards D to the initial base calibration range of Example 16, operation (A). If either standard fails to fall in the range, the calibration is failed.

0 grayscale<median turbidity of A<15 grayscale
240 grayscale<median turbidity of D<255 grayscale
4. Compare the median turbidity of standards A and the median turbidity of standards D to their respective previous calibrations of Example 16 operation (A) using conventional quality control software. If there is an unacceptable amount of deviation between the initial base calibration data value and the field calibration data value, the calibration is failed.
5. If the calibration is not failed, store the median turbidity value of standards A and median turbidity value of standards D for the field instrument and apply these data when calibrating future images obtained with the field instrument of Example 19.

If the calibration is failed, adjust at least one setting on the turbidity measuring instrument and rerun the field turbidity measuring instrument calibration procedure.

Example 19 illustrates a calibration procedure that could be used by, for example, a turbidity measuring instrument manufacturer for transferring calibration from one turbidity measuring instrument to a different field instrument of the same make and model. It is desirable to transfer calibration from one instrument to another in order to be able to more easily compare data from the one instrument to data from the other instrument, for example, when transferring a turbidity measurement protocol (i.e., assay procedure) from a research site that developed the protocol to a manufacturing site or from one manufacturing site to another manufacturing site. In Example 19, the instrument used for field calibration is not the same as the instrument used in Examples 16 to 18. The instrument of Example 19 may be the same make, model and have the same manufacturer as the instrument of Examples 16 to 18 or the instrument of Example 19 may be a different make, model or have a different manufacturer than the make, model or manufacturer of the instrument of Examples 16 to 18, but the instrument of Example 19 functions substantially in the same way and provides substantially the same results when measuring turbidity as the instrument of Examples 16 to 18.

In Examples 16 to 19, if grayscale values for a standard are compared to the reference grayscale values for the standard and the amount of deviation therefrom is deemed to be unacceptable, the turbidity measuring instrument may be adjusted. For example, the photography light source can be adjusted (e.g., a bulb can be changed) or the Nikon Coolpix 5700 camera can be adjusted (e.g., by moving it slightly closer to or farther from the standards, by adjusting the camera's f-stop, shutter speed, or the like. Then the standard is re-measured, and new grayscale values are compared to the reference values for the standard to see if the amount of deviation from the reference values has become acceptable. This process is repeated until the amount of deviation is acceptable.

Example 20

A field calibration procedure for calibrating a field nephelometer using data from an earlier base calibration of the same nephelometer.

A base calibration of a NEPHEL Ostar Microplate Reader nephelometer (instrument) is performed. The Sample Sets 1 to 3 comprising four samples each that are described in Example 16 are employed and turbidity data in FNU of 5 replicate turbidity measurements are obtained for each of the samples. The instrument settings used to obtain the data are recorded. A median base turbidity value in FNU is determined for each sample. A calibration scale is prepared setting a lower limit of 0 FNU and an upper limit of 100 FNU. The sample with the lowest median turbidity value is chosen for the 0 FNU value and the sample with the highest median turbidity value is chosen for the 100 FNU value on the calibration scale. Using the equation that is analogous to the equation described in Example 16, operation (A), a calibration line is plotted by plotting raw turbidity measurement values on an x-axis against calibration scale turbidity values on a y-axis. A slope of the line and a y-intercept are calculated.

Later, a field calibration of the same instrument is performed with Sample Sets 1 and 2 by repeating the 5 replicate turbidity measurements for each of the samples using the same instrument settings as recorded for the base calibration procedure. The 5 raw turbidity values for each of the samples are compared for variability. Also, a median field turbidity value in FNU is determined for each sample. The median turbidity values are compared to the calibration scale obtained with the base calibration procedure. If any of the comparisons reveal an unacceptable magnitude of variability in the data or deviation from base calibration scale, a setting on the field instrument is adjusted and the process is repeated until the magnitude of variability or deviation is acceptable.

The Examples of the invention and the Preparations described herein are for illustration purposes. Using methods analogous to those described therein, it is possible to prepare any single layer or multilayer turbidity standard of the invention without undue experimentation. In general, appropriate ingredients and conditions are substituted for those described in the Examples or Preparations, and any desired minor adjustments such as adding a mixing feature to a polymerization step, carrying out a step with heating or cooling, increasing or decreasing numbers of degassing iterations, increasing or decreasing times, and the like are made. To prepare a single layer or multilayer turbidity standard of the invention, for example, a powdered metal such as powdered aluminum may be substituted for the talc of the relevant above examples; a liquid such as an aqueous solution, motor oil, or the like may be substituted for the water of Example 15; a degassed mixture of a monomer, or two or more monomers, and a polymerization reaction catalyst, with or without a further ingredient such as a polymerization activator/initiator, stabilizer, and the like may be substituted for the degassed mixture of Preparation 2 in the relevant above examples; or any combination thereof.

All references herein to the Periodic Table of the Elements shall refer to the Periodic Table of the Elements published and copyrighted by CRC Press, Inc., 2003. Also, any references to a Group or Groups of elements shall be to the Group or Groups reflected in this Periodic Table of the Elements using the IUPAC system for numbering groups disclosed in, *Nomenclature of Inorganic Chemistry: Recommendations 1990*, G. J. Leigh, Editor, Blackwell Scientific Publications (1990).

All elements and limitations comprising any embodiment of the invention may be independently selected. All journal articles, text books, patents, published patent applications, and unpublished patent applications referenced herein are hereby incorporated by reference in their entireties for any and all purposes.

Illustrative embodiments of the invention are described herein. One of ordinary skill in the art (artisan) would know that supportable changes and modifications may be made to these embodiments without departing from the metes and bounds of the invention as described or claimed herein. The artisan would also know that unsupportable changes or modifications may be made to these embodiments by one of less than ordinary skill in the art that would clearly depart from the metes and bounds of the invention by rendering the invention inoperable for the intended purposes described or claimed herein. In such instances, the artisan would know that the supportable changes and modifications include substituting the phrase "consisting essentially of" or the phrase "consisting of" for any or all occurrences of the term "comprising" used in the description, including the claims, in order to negative any and all such unsupportable changes or modifications.

The invention is hereupon claimed.

What is claimed is:

1. A turbidity calibration standard comprising:
   (a) a number of from 1 to 5 sequentially-interfaced layers, wherein each layer independently comprises a light-permeable polymer or light-permeable interpolymer;
   (b) a measured light transmission modulating amount of at least one light transmission modulator, which is distributed in any one or more of the layers; and
   (c) a light-permeable container, which contains the layers and the at least one light transmission modulator;
wherein the turbidity calibration standard is prepared by a process comprising the following steps:
   (a) independently providing at least one polymerizable monomer;
   (b) optionally, independently providing a light transmission modulator;
   (c) if a light transmission modulator is provided in step (b), distributing the light transmission modulator in the at least one polymerizable monomer to give a mixture of the light transmission modulator distributed in the at least one polymerizable monomer;
   (d) adding the at least one polymerizable monomer of step (a) and, if provided, the light transmission modulator of step (b) or adding the mixture of step (c) to a light-permeable container;
   (e) polymerizing the at least one polymerizable monomer in the light-permeable container to yield a first layer comprising a first light-permeable polymer or a first light-permeable interpolymer, and, optionally, a light transmission modulator distributed in the first light-permeable polymer or the first light-permeable interpolymer; and
   (f) repeating steps (a) to (e) from 0 to 4 more times, each time independently selecting at least one polymerizable monomer and, optionally, a light transmission modulator to further yield second to fifth layers, respectively;
wherein at least one of the first to fifth light-permeable layers contains a light transmission modulator distributed therein.

2. The standard according to claim 1, wherein the number of layers is 1.

3. The standard according to claim 1, wherein the number of layers is 2 or 3.

4. The standard according to claim 1, wherein each layer comprises a light-permeable polymer, copolymer, or terpolymer.

5. The standard according to claim 1, wherein the light-permeable polymer comprises a light-permeable: acrylic polymer, epoxy polymer, high density polyethylene, polycarbonate, polyester, polymethylmethacrylate, polystyrene, polyurethane, polyvinylchloride, polysiloxane polymer, or silicone polymer.

6. The standard according to claim 1, wherein the light-permeable interpolymer is a copolymer comprising a light-permeable styrene-methylmethacrylate copolymer or light-permeable styrene-acrylonitrile copolymer or the light-permeable interpolymer is a terpolymer comprising a light-permeable ethylene propylene diene terpolymer.

7. The standard according to claim 1, wherein at least one of the at least one light transmission modulator comprises a solid domain.

8. The standard according to claim 7, wherein the solid domain is a pigment that is a powdered carbon black, powdered ferric-ferrocyanide, powdered cadmium sulfide, a powdered metal, a powdered metal carbonate, a powdered metal oxide, or a powdered silicate.

9. The standard according to claim 1, wherein each one of the at least one light transmission modulator comprises a solid domain.

10. The standard according to claim 1, wherein at least one of the at least one light transmission modulator comprises a liquid domain.

11. The standard according to claim 10, wherein the at least one liquid domain comprises water, olive oil, soybean oil, safflower oil, fish oil, medium-chain triglyceride oil, liquid milk fats, a silicone-based oil, gasoline, motor oil, diesel fuel, kerosene, crude oil, hydraulic oil, or lubricant oil.

12. The standard according to claim 1, wherein the measured light transmission modulating amount is from 0.002 Formazin Nephelometric Units (FNU) to 100,000 FNU.

13. A method of calibrating a turbidity measuring instrument, the method comprising the following steps:
   (a) providing a turbidity calibration standard according to claim 1 and a turbidity measuring instrument;
   (b) measuring turbidity of the turbidity calibration standard with the turbidity measuring instrument to produce a reference value of turbidity;
   (c) at a time after step (a), measuring turbidity of the turbidity calibration standard with the turbidity measuring instrument to produce a test value of turbidity;
   (d) determining a magnitude of deviation of the test value of turbidity from the reference value of turbidity;
   (e) adjusting, if necessary, at least one setting of the turbidity measuring instrument based on the determination of step (d);
   (f) repeating steps (c) to (e) until the magnitude of deviation is acceptable.

14. A method of transferring turbidity calibration from a first turbidity measuring instrument to a second turbidity measuring instrument, the method comprising the following steps:
   (a) providing a turbidity calibration standard according to claim 1, a first turbidity measuring instrument, and a second turbidity measuring instrument, wherein the first and second turbidity measuring instruments are different;
   (b) measuring turbidity of the turbidity calibration standard with the first turbidity measuring instrument to produce a reference value of turbidity;
   (c) measuring turbidity of the turbidity calibration standard with the second turbidity measuring instrument to produce a test value of turbidity;
   (d) determining a magnitude of deviation of the test value of turbidity from the reference value of turbidity;
   (e) adjusting, if necessary, at least one setting of the second turbidity measuring instrument based on the determination of step (d);
   (f) repeating steps (c) to (e) until the magnitude of deviation is acceptable.

15. A process for preparing a turbidity calibration standard according to claim 1, the process comprising the following steps:

(a) independently providing at least one polymerizable monomer;
(b) optionally, independently providing a light transmission modulator;
(c) if a light transmission modulator is provided in step (b), distributing the light transmission modulator in the at least one polymerizable monomer to give a mixture of the light transmission modulator distributed in the at least one polymerizable monomer;
(d) adding the at least one polymerizable monomer of step (a) and, if provided, the light transmission modulator of step (b) or adding the mixture of step (c) to a light-permeable container;
(e) polymerizing the at least one polymerizable monomer in the light-permeable container to yield a first layer comprising a first light-permeable polymer or a first light-permeable interpolymer, and, optionally, a light transmission modulator distributed in the first light-permeable polymer or the first light-permeable interpolymer; and
(f) repeating steps (a) to (e) from 0 to 4 more times, each time independently selecting at least one polymerizable monomer and, optionally, a light transmission modulator to further yield second to fifth layers, respectively;

wherein at least one of the first to fifth light-permeable layers contains a light transmission modulator distributed therein.

16. A kit comprising a turbidity calibration standard according to claim 1; information about a turbidity measurement of the turbidity calibration standard measured with a first turbidity measuring instrument; and instructions for use of the standard in calibrating the first turbidity measuring instrument or instructions for transferring turbidity calibration from the first turbidity measuring instrument to a second turbidity measuring instrument.

* * * * *